United States Patent [19]
Berzofsky et al.

[11] Patent Number: 5,980,899
[45] Date of Patent: Nov. 9, 1999

[54] IDENTIFICATION OF PEPTIDES THAT STIMULATE HEPATITIS C VIRUS SPECIFIC CYTOTOXIC T CELLS

[75] Inventors: Jay A. Berzofsky, Bethesda; Mutsunori Shirai, Rockville; Toshitaka Akatsuka, Chevy Chase, all of Md.; Stephen M. Feinstone, Washington, D.C.

[73] Assignee: The United States of America as represented by the Department of Health and Human Services, Washington, D.C.

[21] Appl. No.: 07/894,063

[22] Filed: Jun. 10, 1992

[51] Int. Cl.⁶ .......................... A61K 39/00; A61K 39/12; A61K 39/29; C07K 2/00
[52] U.S. Cl. .................................... 424/185.1; 424/186.1; 424/189.1; 424/204.1; 424/228.1; 530/300; 530/324; 530/325; 530/326; 530/327; 530/328
[58] Field of Search .................................. 424/89, 228.1, 424/185.1, 186.1, 189.1, 204.1; 530/324, 325, 326, 327, 328, 300

[56] References Cited

U.S. PATENT DOCUMENTS 4,861,588   8/1989   Neurath et al. .
4,879,213  11/1989   Fox et al. .

FOREIGN PATENT DOCUMENTS 0 318 216   6/1989   European Pat. Off. .
0 468 527   1/1992   European Pat. Off. .

OTHER PUBLICATIONS

Battegay et al (Journal of Virology, vol. 69, No. 4, pp. 2462–2470), Apr. 1995.
Nozaki et al Chemical Abstracts, 116(1), Jan. 6, 1992, Columbus, Ohio, US; abstract No. 4784.
Boon et al., "Teaching the Immune System To Fight Cancer," *Scientific American* 266(3): 82–89 (1993).
Schulz et al., "Peptide–Induced Antiviral Protection By Cytotoxic T Cells," *P.N,A.S., USA* 88: 991–993 (1991).
Kast et al., "Protection Against Lethal Sendai Virus Infection By in vivo Priming Of Virus–Specific Cytotoxic T Lymphocytes With A Free Synthetic Peptide," *P.N.A.S., USA* 88: 2283–2287 (1991).
Berzofsky, J. "Antigenic Peptide Interaction With MHC Molecules: Implications For The Design of Artifical Vaccines," *Seminars in Immunology* 3: 203–216 (1991).
Feinstone et al., "Non–A, Non–B, Hepatitis in Chimpanzees and Marmosets," *The Journal of Infectious Diseases* vol. 144, No. 6, pp. 588–598 (Dec. 1981).
Realdi et al., "Long–term Follow–up of Acute and Chronic Non–A, Non–B Post–Transfusion Hepatitis: Evidence of Progression to Liver Cirrhosis," *Gut*, vol. 23, pp. 270–275 (1982).

Takahashi et al., "An Immunodominant Epitope of the Human Immunodeficiency Virus Envelope Glycoprotein gp 160 Recognized by Class 1 Major Histocompatibility Complex Molecule–Restricted Murine Cytotoxic T Lymphocytes," *Proc. Natl. Acad. Sci. USA*, vol. 85, pp. 3105–3109 (May 1988).
Choo et al., "Isolation of a cDNA Clone Derived from a Blood–Borne Non–A, Non–B Viral Hepatitis, Genome," *Science*, vol. 244, pp. 359–362 (Apr. 1989).
Kuo et al., "An Assay for Circulating Antibodies to a Major Etiologic Virus of Human Non–A, Non–B Hepatitis," *Science*, vol. 244, pp. 362–364 (Apr. 1989).
Imawari et al., "Establishment of a Human T–Cell Clone Cytotoxic for Both Autologous and Allogeneic Hepatocytes from Chronic Hepatitis Patients with Type Non–A, Non–B, Virus," *Proc. Natl. Acad. Sci. USA*, vol. 86, pp. 2883–2887 (Apr. 1989).
Takahashi et al., "A Single Amino Acid Interchange Yields Reciprocal CTL Specificities for HIV–1 gp 160," *Science*, vol. 246, pp. 118–121 (Oct. 1989).
Alter et al., "Detection of Antibody to Hepatitis C Virus in Prospectively Followed Transfusion Recipients with Acute and Chronic Non–A, Non–B Hepatitis," *N. Engl. J. Med.*, vol. 321, No. 22, pp.1494–1500 (Nov. 1989).
Takahashi et al., "Structural Requirements for Class 1 MHC Molecule–Mediated Antigen Presentation and Cytotoxic T Cell Recognition of an Immunodominant Determinant of the Human Immunodeficiency Virus Envelope Protein," *the Journal of Experimental Medicine*, vol. 170, pp. 2023–2035 (Dec. 1989).
Hosmalin et al., "An Epitope in Human Immunodeficiency Virus 1 Reverse Transcriptase Recognized by Both Mouse and Human Cytotoxic T Lymphocytes," *Proc. Natl. Acad. Sci. USA*, vol. 87, pp. 2344–2348 (1990).

(List continued on next page.)

*Primary Examiner*—Anthony C. Caputa
*Assistant Examiner*—Mark Navarro
*Attorney, Agent, or Firm*—Needle & Rosenberg, P. C.

[57] ABSTRACT

The cytotoxic T cell response to the protein encoded by the NS5 region of hepatitis C virus was determined using 28 peptides from NS5 which were selected by an amphipathicity algorithm as candidates for T cell epitopes. In BALB/c mice, a single relatively conserved epitope represented by a 16-residue synthetic peptide was presented by $D^d$ class I major histocompatibility complex (MHC) molecules to conventional $CD4^-CD8^+$ CTL. An exemplary peptide, which represents amino acid residues 2422–2437 of the polyprotein of the Chiron HCV1 isolate, had the amino acid sequence MSYSWTGALVTPCAAE [SEQ ID NO: 1]. A CTL line specific for this peptide recognized the two known natural variants of this NS5 sequence, each with conservative substitutions. Thus, CTL can recognize the product of the HCV NS5 gene, the probable RNA polymerase, in association with class I MHC molecules on model target cells and may recognize the same epitope on hepatocytes or any other cells infected with the virus.

7 Claims, 8 Drawing Sheets

OTHER PUBLICATIONS

Maéno et al., "A cDNA Clone Closely Associated with Non–A, Non–B Hepatitis," *Nucleic Acids Research*, vol., 18, No. 9, pp. 2685–2689 (1990).

Kiyosawa et al., "Interrelationship of Blood Transfusion, Non–A, Non–B Hepatitis and Hepatocellular Carcinoma: Analysis by Detection of Antibody to Hepatitis C Virus," *Hepatology*, vol. 12, No. 4, pp.671–675 (1990).

Kato et al., "Molecular Cloning of the Human Hepatitis C Virus Genome from Japanese Patients with Non–A, Non–B Hepatitis," *Proc. Natl. Acad. Sci. USA*, vol. 87, pp. 9524–9528 (Dec. 1990).

Van Der Poel et al., "Confirmation of Hepatitis C Virus Infection by New Four–Antigen Recombinant Immunoblot Assay," *The Lancet*, vol. 337, pp. 317–319 (Feb. 1991).

Takamizawa et al., "Structure and Organization of the Hepatitis C Virus Genome Isolated from Human Carriers," *Journal of Virology*, vol. 65, No. 3, pp. 1105–1113 (Mar. 1991).

Berzofsky, "Approaches and Issues in the Development of Vaccines Against HIV," *Journal of Acquired Immune Deficiency Syndromes*, vol. 4, No. 5, pp. 451–459 (1991).

Christiano et al., "Hepatitis C Viral RNA in Serum of Patients with Chronic Non–A, Non–B Hepatitis: Detection by the Polymerase Chain Reaction Using Multiple Primer Sets," *Hepatology*, vol. 14, No. 1, pp. 51–55 (1991).

Ogata et al., "Nucleotide Sequence and Mutation Rate of the H Strain of Hepatitis C Virus," *Proc. Natl. Acad. Sci. USA*, vol.88, pp. 3392–3396 (Apr. 1991).

Falk et al., "Allele–specific Motifs Revealed by Sequencing of Self–peptides Eluted from MHC Molecules," *Nature*, vol. 351, pp. 290–296 (May 1991).

Houghton et al., "Molecular Biology of the Hepatitis C Viruses: Implications for Diagnosis, Development and Control of Viral Diseases," *Hepatology*, vol. 14, No. 2, pp.381–388 (1991).

Weiner et al., "Variable and Hypervariable Domains are Found in the Regions of HCV Corresponding to the Flavivirus Envelope and NS1 Proteins and the Pestivirus Envelope Glycoproteins," *Virology*, vol. 180, pp. 842–848 (1991).

Jardetzky et al., "Identification of Self Peptides Bound to Purified HLA–B27," *Nature*, vol. 353, pp. 326–329 (Sep. 1991).

Romero et al., "H–2K$^d$–restricted Antigenic Peptides Share a Simple Binding Motif," *J. Exp. Med.*, vol. 174 pp. 603–612 (Sep. 1991).

Hunt et al., "Characterization of Peptides Bound to the Class 1 MHC Molecule HLA–A2.1 by Mass Spectrometry," *Science*, vol. 255, pp. 1261–1263 (Mar. 1992).

Mester et al. Rev. Inf. Dis. 13:5935–45 1991.

Kumar et al. PNAS 87: 1337–1341 Feb. 1990.

Paul et al. "Fundamental Immunology". published by Raven Press (NY) 1993 see pages 1222–1223.

Rouse et al. Antiviral Cytotoxic . . . 1988 pp.16–33 J. Inf. Dis 10(1):.

Buddey et al. Monoclonal antibodies identify the NS5 . . . J. Gen Virol 73 pp. 1125–30 May 1992.

Yewdell et al. Influenza A virus nucleoprotein . . . PNAS 82 pgs. 1785–89 1985.

Cornette et al. Identification of a T cell epitope . . . 1989. 611–634, Methods in Enzymology (178).

Delisi et al. T cell antigenic sites . . . 1985. 7048–52 PNAS 82.

Bangham et al. Human and Murine Cytotoxic T cells . . . 1986. 3973–77. J. Immunol. 137.

Clerici et al. Detection of Cytotoxic T Lymphocytes . . . Mar. 1991. 2214–2219. J. Immunol. 146.

Lauer et al. Current Communications in Molecular Biology 1985. See pp. 71–76, and pp. 156–159.

Vaccines 88, New Chemical Approaches and Genetic Approaches to Vaccination Francis et al. pp. 1–7.

Vaccines 87, Modern Approaches to New Vaccines Francis et al. pp. 60–67.

FIG. 1A

| Peptide | Residue Nos. | Sequence | Amphipathic Score |
|---|---|---|---|
| 3 | (1958-1977) | RRLHQWISSECTTPCSGSWL | 18.0 |
| 4 | (1969-1988) | TTPCSGSWLRDIWDWICEVL | 26.8 |
| 5 | (1981-2000) | WDWICEVLSDFKTWLKAKLM | 22.6 |
| 6 | (2042-2061) | GTMRIVGPRTCRNMWSGTFP | 20.8 |
| 7 | (2089-2103) | RVSAEEYVEIRQVGDFHYV<u>T</u><br>         R         S | 25.9 |
| 8 | (2089-2108) | EYVEIRQVGDFHYV<u>T</u>GMTTD<br>              S | 23.9 |
| 9 | (2113-2132) | PCQ<u>V</u>PSPEFFTELDGVRLHR<br>   I | 18.1 |
| 10 | (2117-2136) | PSPEFFTELDGVRLHRFAPP | 24.1 |
| 11 | (2168-2183) | VAVLTSMLTDPSHITA | 14.1 |
| 12 | (2180-2195) | ITAEAAGRRLARGSP | 11.2 |
| 13 | (2265-2284) | ER<u>A</u>ISVPAEILRKSRRFAQA<br>   E | 19.6 |
| 14 | (2267-2286) | <u>A</u>ISVPAEILRKSRRFAQALP<br>E | 19.3 |
| 15 | (2335-2354) | LTESTLSTALAELATRSFGS | 22.1 |
| 16 | (2348-2362) | ATRSFGSSSTSGITG | 8.3 |
| 17 | (2422-2437) | MSY<u>S</u>WTGALVTPCAAE | 13.2 |
| 17FDA | | MSYTWTGALVTPCAAE | |
| 17JPN | | MSYTWTGAL<u>I</u>TPCAAE | |
| 18 | (2438-2455) | EQKLPINALSNSLLRHHN | 16.1 |
| 19 | (2477-2497) | LQVLDSHYQDVLKEVKAAASK | 29.8 |
| 20 | (2531-2550) | H<u>A</u>RKAVTHINSVWKDLLED<u>N</u><br> V                  S | 28.0 |
| 21 | (2535-2554) | AV<u>T</u>HINSVWKDLLED<u>NV</u>TPI<br>  A            SF | 28.7 |
| 22 | (2583-2598) | PDLGVRVCEKMALYDV | 12.2 |
| 23 | (2593-2607) | MALYDVV<u>T</u>KLPLAVM<br>       S | 11.1 |
| 24 | (2668-2683) | QARVAIKSLTERLYVG | 11.1 |
| 25 | (2701-2719) | ASGVLTTSCGNTLTCYIKA | 17.5 |
| 26 | (2721-2736) | AA<u>C</u>RAAGLQDCTMLVC<br>  R | 12.7 |
| 27 | (2749-2768) | VQEDAASLRAFTE<u>A</u>MTRYS<u>A</u><br>             V      V | 27.3 |
| 28 | (2757-2776) | RAFTEAMTRYS<u>A</u>PPGDPPQP<br>          V | 24.3 |
| 29 | (2822-2834) | HTPVNSWLGNIIM | 11.2 |
| 31 | (2866-2880) | EIY<u>G</u>ACYSIEP<u>L</u>DLP<br>   A        V | 12.0 |

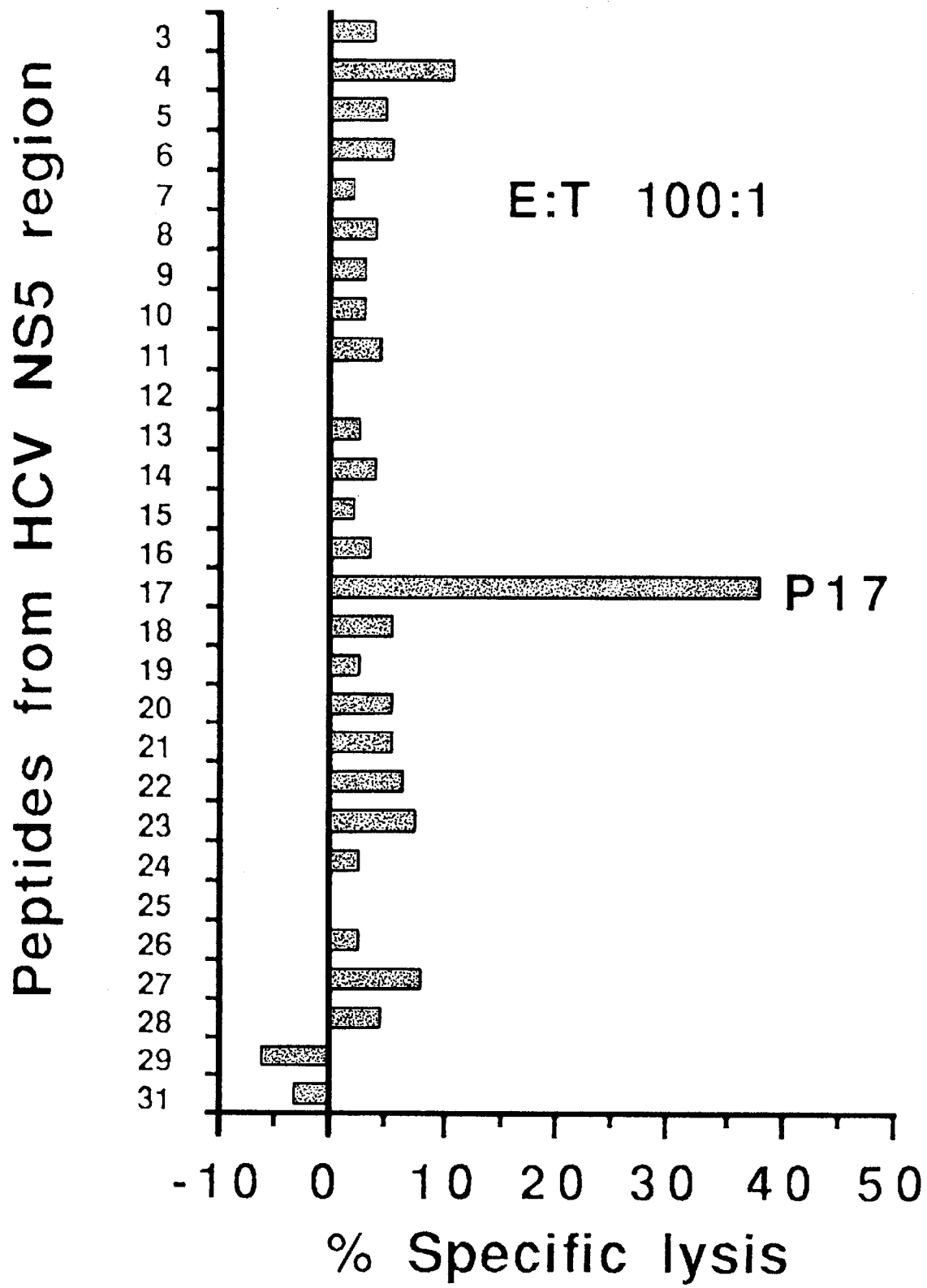
FIG. IB(1)

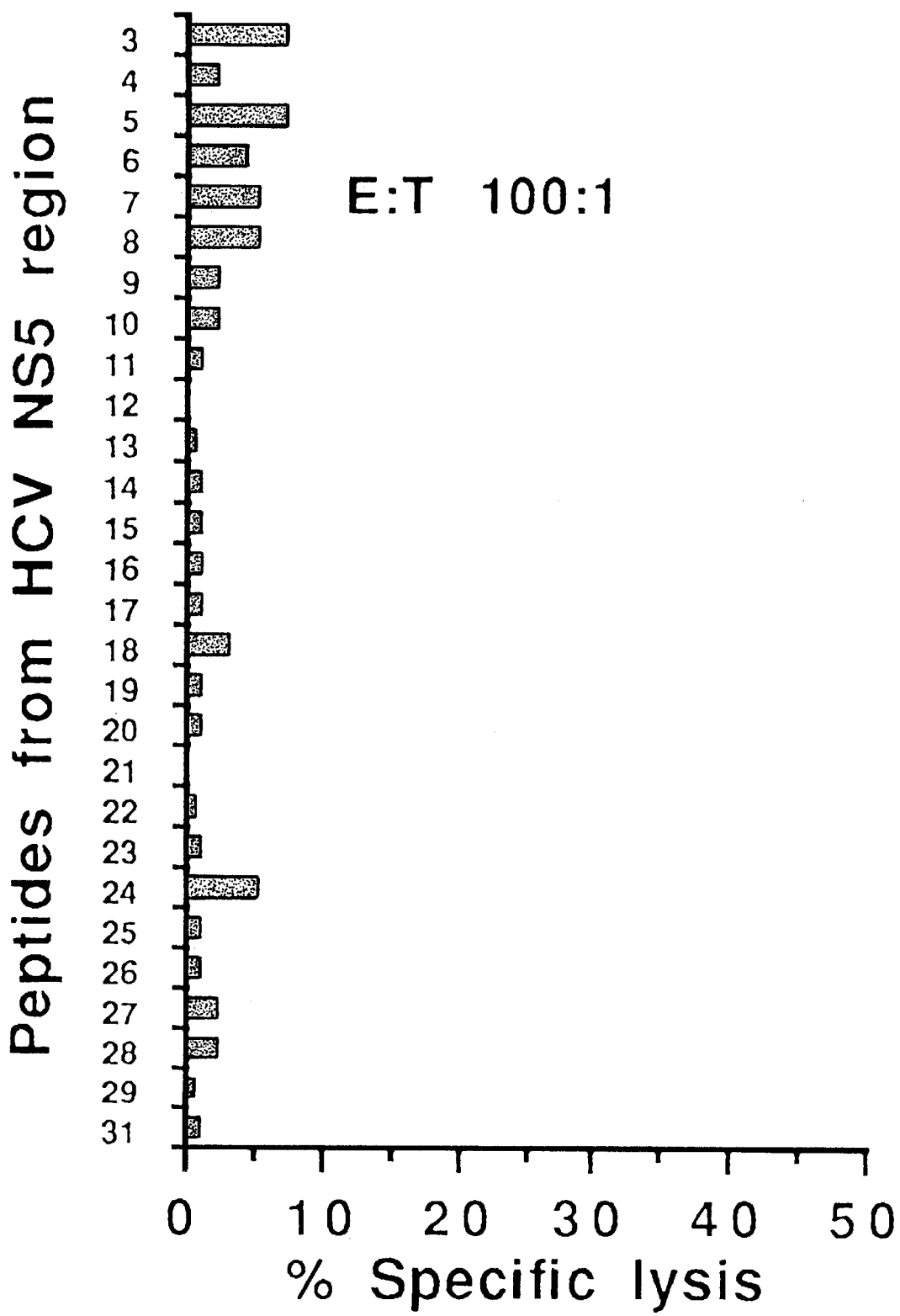
FIG. 1B(2) BALB.B

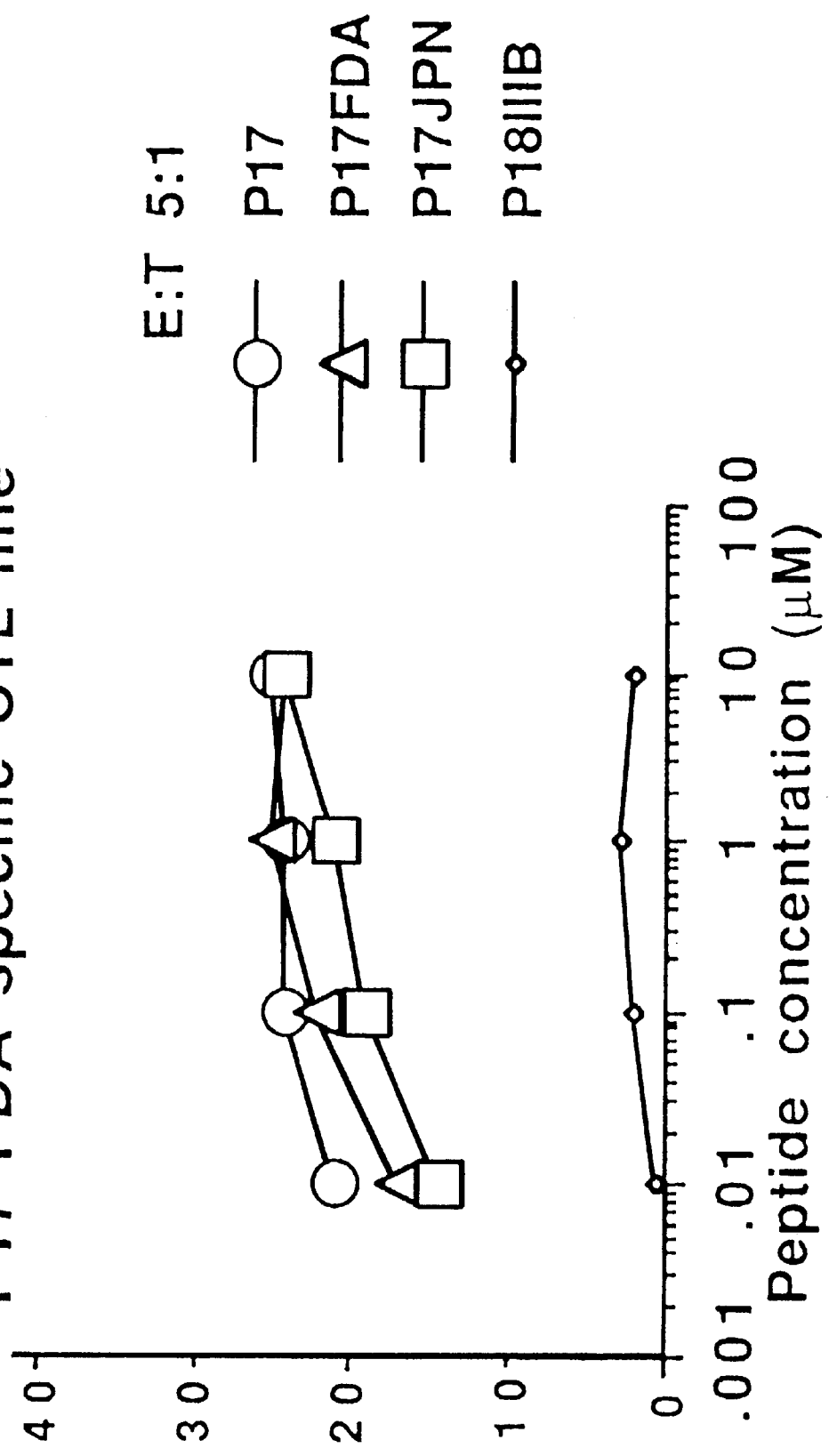

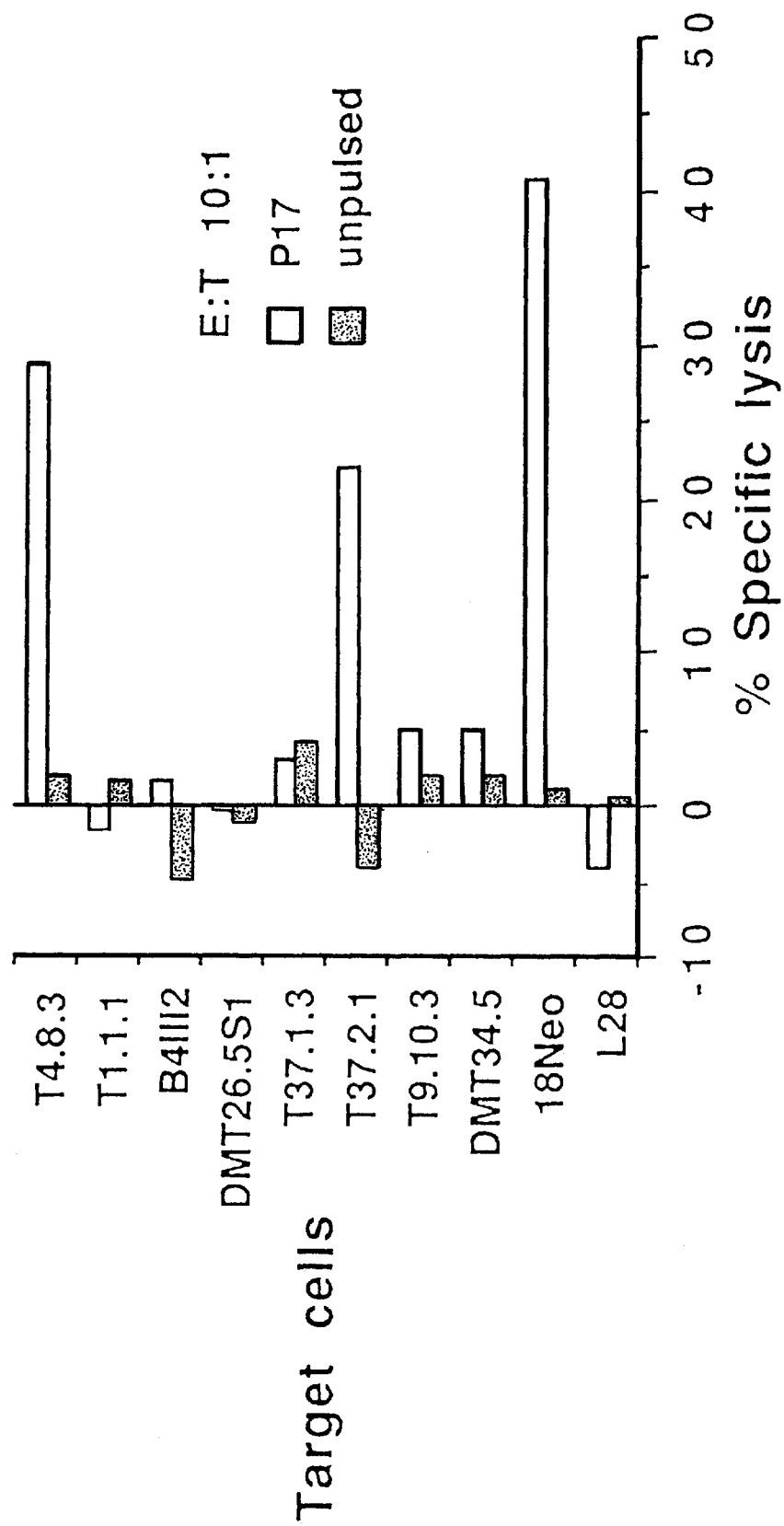

IDENTIFICATION OF PEPTIDES THAT STIMULATE HEPATITIS C VIRUS SPECIFIC CYTOTOXIC T CELLS

BACKGROUND OF THE INVENTION

Hepatitis C virus (HCV) is the recently recognized causative agent of parenterally transmitted non-A, non-B (NANB) hepatitis. The RNA genome of the virus has been molecularly cloned from the plasma of an experimentally infected chimpanzee (see document number 8 in the list of numbered documents at the end of the specification). Analysis of the sequence of the genome revealed that it is a single-stranded, plus sense RNA of approximately 9500 nucleotides in length. A single long open reading frame of 9033 nucleotides was found, coding for a polyprotein of 3011 amino acid residues. These genomic features and sequence comparisons, combined with knowledge about the size and lability to lipid solvents, indicated that the virus is probably a member of the Flavivirus family (6,22). However, it may be more closely related to the pestivirus genus than classic flaviviruses (27,60).

Based on sequence similarities of both the genome and the predicted polyprotein, as well as on certain features of the polyprotein such as hydrophobicity profiles and acidic/basic amino acid content, it is predicted that proteins of HCV are encoded in the same general regions of the genome as has been determined for the flaviviruses. In the flaviviruses and the related pestiviruses, approximately the amino-terminal one third of the polyprotein constitutes the structural proteins of the virus. These consist of a highly basic nucleocapsid protein termed "C," an envelope-associated glycoprotein termed "M" and a second envelope glycoprotein "E." The non-structural proteins are named NS1 through NS5, but the functions of only NS3 and NS5 have been assigned with certainty. NS3 is the viral protease and probably a helicase, and NS5 is the viral RNA-dependent RNA polymerase.

The HCV polyprotein is processed in a series of proteolytic digestions by a combination of the viral protease and host signalase. The processing of the pestivirus polyprotein is different in detail from that of the flaviviruses, but is similar in its general scheme. The proteins of HCV have been determined largely by analogy with the flavivirus proteins, and, like the pestiviruses, they may also differ in details of size, number, and processing from the flaviviruses. With these caveats, for convenience of nomenclature but not to imply identity in function or processing, hereafter the nonstructural region under study that is analogous to the flavivirus NS5 region RNA polymerase is referred to as the "NS5 region" or "NS5 protein" of HCV.

Diagnostic tests based on expressed viral antigens have been developed and seroepidemiologic surveys using these assays have been performed (33). Studies on the immune response to HCV infections are still at a formative stage. The commercially available antibody assay measures antibody to an HCV antigen expressed in yeast by recombinant DNA technology. This antigen, termed "C100-3", is derived from the non-structural protein coding region of the viral genome and probably represents a portion of NS4 (33). Newer versions of the assay include antigens from NS3 (protease/helicase) and the internal nucleocapsid protein, C (64). None of these antibodies is thought to be protective, but each is commonly found in chronically infected individuals.

HCV is not only the cause of most cases of parenterally acquired non-B hepatitis, but also is responsible for a large portion of sporadic community acquired acute viral hepatitis, chronic hepatitis of unknown origin, as well as cryptogenic cirrhosis and probably hepatocellular carcinoma (2,16,31,50). It is the propensity of this virus to cause chronic infections and chronic liver disease that makes it such a medically important problem. Treatment of chronic HCV liver disease by α-interferon therapy has recently been approved by the Food and Drug Administration (FDA) in the United States. However, less than half the patients respond, and of the responders approximately 50% relapse after treatment is stopped (16).

Accordingly, there is an important need for a vaccine to protect against infection by this virus. While the present diagnostic tests are based on detection of serum antibody to expressed viral proteins, to date all proteins recognized by such antibodies have represented either non-structural viral proteins or internal components of the virus particle. It is not clear whether effective neutralizing antibodies to HCV are commonly produced by individuals infected with the virus.

Cytotoxic T lymphocytes (CTL) have been found to mediate protection in vivo against certain virus infections (17,47,48). In hepatitis B infection, CTL are thought to be responsible for the pathogenesis of chronic type B hepatitis and to lyse hepatitis B-virus-infected hepatocytes by recognizing the viral antigen expressed on infected cells (39,42). In the case of HCV, there is no information on the pathogenesis of viral infections. The chronicity of HCV infections as well as histopathologic findings indicate that the virus is probably not directly cytopathic (or cytolytic) in hepatocytes. It is possible that the chronic liver disease associated with HCV infections is immune mediated.

These observations provide reason to believe that CTL specific for HCV may be involved causally in the pathogenesis of HCV-related disease, or that cellular immunity is important for protection or recovery from infection. Previous studies have reported that $CD8^+$ CTL recognize hepatocytes from patients with chronic NANB hepatitis (28). To date, however, no epitope of HCV recognized by T cells has been identified in any HCV protein.

Accordingly, there is a need to identify an epitope of HCV that is recognized by T cells. Peptides comprising such an epitope can be used to determine the role of CTL in HCV infection and pathogenesis. Thus, such peptides may be used to modulate the HCV-specific CTL response in treatment of the hepatitis or other HCV-related disease, by enhancing a protective effect or blocking a pathogenic effect. In addition, such peptides may be used in a vaccine to prevent infection, by stimulating a protective CTL response.

In other viral models, internal proteins are the major targets of the CTL response (3,30,49,62,69). In previous studies by the present inventors and others, the peptides from an internal protein, reverse transcriptase, of HIV as well as envelope glycoprotein and gag and nef proteins were recognized by CTL in the mouse and human (10,14,24,32,43,57,65). Immunization with the envelope protein may not be practical for HCV because the envelope is relatively highly variable in sequence (27). Therefore, CTL clones may distinguish different isolates of HCV, as has been shown in HIV-1 studies (41,58,59).

In contrast to the substantial amino acid sequence variation in the predicted envelope glycoproteins of HCV (designated "E1" and "E2/NS1"), the internal nucleocapsid proteins, C, nonstructural (NS) region 3, NS4, and NS5 proteins all show greater sequence conservation among HCV isolate groups (27). The coding region of the HCV genome that is analogous to NS5 of the flaviviruses by both its location in the genome and its sequence similarities, is believed to represent the viral replicase.

SUMMARY OF THE INVENTION

It is therefore an object of the present invention to provide a peptide that induces cytotoxic T cells specific for HCV. It is a further object of this invention to provide a method of detecting cytotoxic T lymphocytes that recognize an epitope of NS5 protein of hepatitis C virus. It is a still further object of the invention to provide a method of provoking in a mammal an immune response to NS5 protein of hepatitis C virus. Ultimately, it is an object of the present invention to provide a vaccine to protect against infection by hepatitis C virus.

In achieving these objects, there has been provided, in accordance with one aspect of this invention, a purified peptide that displays a T cell epitope which induces a cytotoxic T cell response in lymphocytes of a mammal against cells expressing hepatitis C virus NS5 protein, wherein said peptide comprises at least about eight consecutive residues of an amino acid sequence selected from the group consisting of MSYSWTGALVTPCAAE [SEQ ID NO: 1], MSYTWTGALVTPCAAE [SEQ ID NO: 2], MSYTWTGALITPCAAE [SEQ ID NO: 3] and immunological equivalents thereof. In various embodiments of this aspect of the invention, the peptide further displays an additional T cell epitope, either for a cytotoxic T cell or a helper T cell, or a B cell epitope (antibody recognition site).

According to another aspect of this invention, there has been provided a method of detecting in lymphocytes of a mammal cytotoxic T cells that respond to a T cell epitope of NS5 protein of hepatitis C virus, comprising the steps of: (a) contacting target cells with a peptide according to claim 1, wherein said target cells are MHC-compatible with lymphocytes to be tested for said cytotoxic T cells; (b) incubating said lymphocytes to be tested for said cytotoxic T cells with a peptide according to claim 1; and (c) determining whether said lymphocytes exert a cytotoxic effect on said target cells, thereby indicating the presence of said lymphocytes that recognize a T-cell epitope of NS5 protein of hepatitis C virus.

Yet another aspect of the present invention provides a method of provoking in a mammal an immune response to NS5 protein of hepatitis C virus comprising a step of administering to said mammal an amount of a peptide according to claim 1 that is effective for inducing a cytotoxic T cell response against cells expressing hepatitis C virus NS5 protein.

Still another aspect of the present invention provides a vaccine that protects against infection by or reduces pathogenic effects of hepatitis C virus, where the vaccine comprises a peptide according to this invention.

Additional objects and advantages of the invention will be set forth in part in the description that follows, and in part will be obvious from the description, or may be learned by practice of the invention. The objects and the advantages of this invention may be realized and obtained by means of the compositions of matter and processes particularly pointed out in the appended claims.

BRIEF DESCRIPTION OF THE DRAWINGS

FIG. 1A illustrates the sequences (SEQ ID NOS. 4–17, 1–3, and 18–31) of a series of 28 peptides selected by an amphipathicity algorithm as candidates for T cell epitopes from the HCV NS5 region. The sequences of synthesized peptides are based on the isolate of Chiron Corporation which was made in the U.S.A. (26), except for two P17 variants, P17FDA, which is based on an isolate made at the U.S. FDA and P17JPN, based on two isolates obtain independently in different Japanese laboratories). Residues at which the FDA isolate differs from the Chiron sequence are shown under the original sequences with underlines. Amphipathic scores (35) of the peptides are indicated.

FIG. 1B depicts cytotoxic T lymphocyte responses to peptides from HCV NS5 in BALB/c and BALB.B mice. Mice were primed intravenously with $10^7$ plaque-forming units of recombinant vaccinia virus expressing the HCV NS5 region (vHCV). The immune spleen cells were restimulated in vitro with peptides at 4 $\mu$M (3 different peptides for each culture) in the presence of supernatant of lymphocytes stimulated with Con A (containing IL-2), and cells treated with IL-2 but no peptide were included as controls. CTL activity was measured against 3T3 fibroblast cells transfected with a neo resistance gene (18Neo, H-$2^d$ class I positive, class II negative) in BALB/c and EL-4 (H-$2^b$) in BALB.B. Targets were sensitized with 10 $\mu$M of each peptide or no peptide for 6 hours. The experiments were performed in triplicate. Effector:target (E:T) ratio=100:1, 5000 target cells/well. Lysis in the absence of peptide was 2.2–7.7% in BALB/c (4.2% for P17 stimulated immune cells) and less than 2% in BALB.B. In general, standard errors of triplicates were <5% of the values, and comparable results were obtained in a repeated experiment.

FIG. 5 illustrates identification of the MHC class I molecules responsible for presentation of P17 to the CTL line in the H-$2^d$ strain. Target cells were pulsed overnight with P17 (10 $\mu$M) and washed three times. Effector:Target ratio=10:1. TM: transmembrane portion of the $D^d$ molecule. The origin of α1 α2 α3 TM for each transfectant is $D^d D^d D^d D^d$, T4.8.3; $L^d L^d L^d L^d$, T1.1.1; $-D^d D^d D^d$, DMT26.5S1; $D^d D^d L^d L^d$, T37.2.1; $L^d L^d D^d D^d$, T37.1.3; $D^d L^d L^d L^d$, T9.10.3; and $L^d D^d D^d D^d$, DMT34.5. Standard errors of triplicates were generally <5% of the values, and comparable results were obtained in two independent experiments. L28: DAP3 L cell ($H-2^k$) transfected with pSV2neo gene alone; 18Neo: BALB/c 3T3 fibroblast ($H-2^d$) transfected with PSV2NEO alone.

DETAILED DESCRIPTION OF SPECIFIC EMBODIMENTS

Figure 2A:
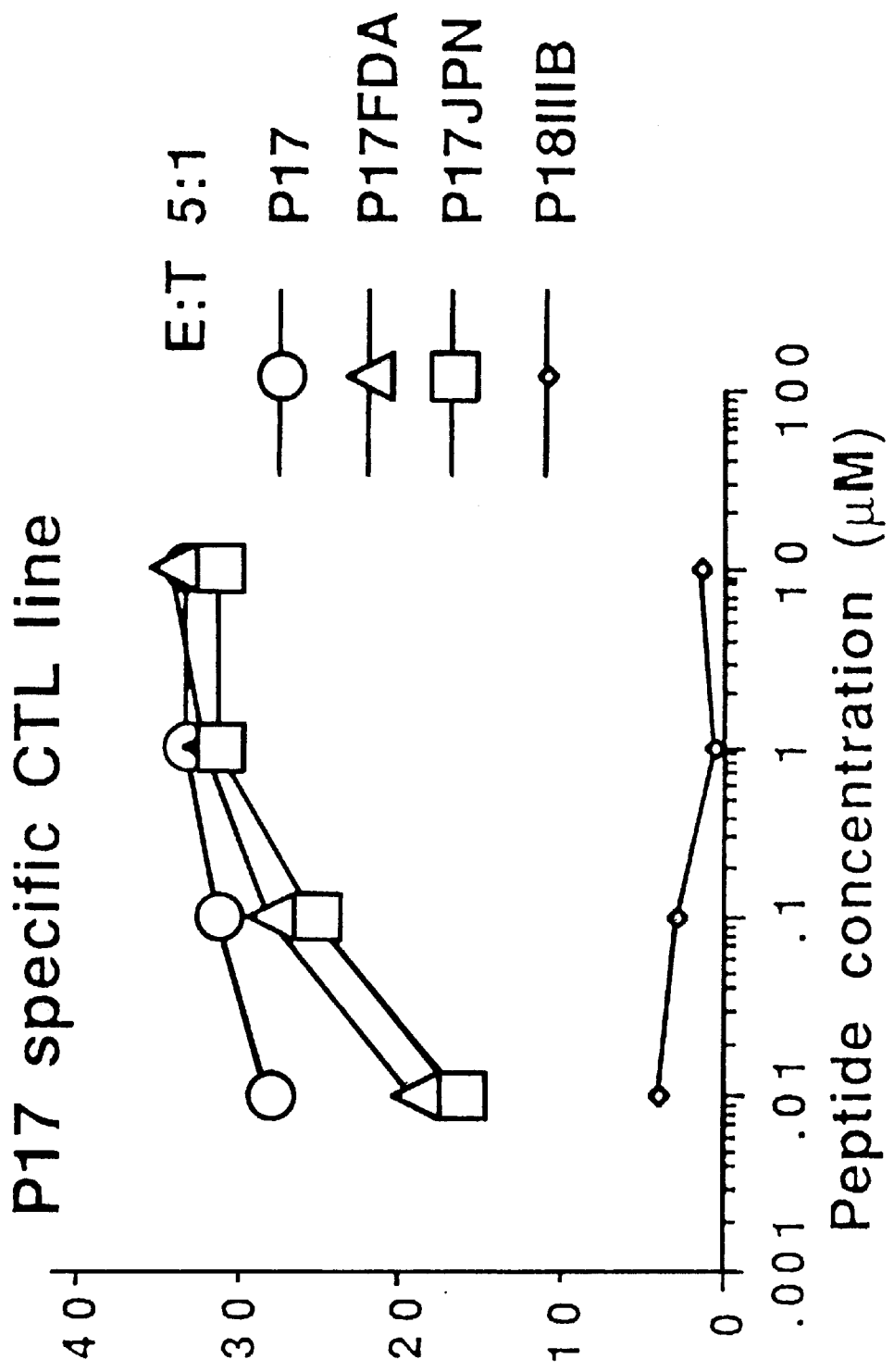
FIG. 2 shows the cytotoxicity of CTL lines specific for P17 and P17FDA against each specific peptide and other P17 variants. The effects of single amino acid mutation on recognition of variant epitopes was examined. $5 \times 10^3$ $^{51}$Cr-labelled target cells (18Neo) were cultured with effector cells from long-term CTL lines, repetitively stimulated with specific peptides, in the presence of each specific peptide, other P17 variants, P18IIIB (negative control peptide) or no peptide. E:T, effector:target ratio. Lysis in the absence of peptide was <1%. Standard errors of triplicates were generally <5% of the values, and comparable results were obtained in three independent experiments.

As mentioned above, it was known heretofore that CTL mediate protection in vivo against certain virus infections, but no CTL epitopes have yet been defined in any HCV protein. Nevertheless, it has been discovered that the nonstructural protein of HCV which corresponds to the flavivirus gene (NS5) having homology to RNA polymerase is a relatively conserved target protein for CTL, and, in fact presents an epitope that induces a cytotoxic T cell response in lymphocytes.

To investigate the epitope specificity of CTL specific for the HCV NS5 protein, 28 peptides from this protein were tested in murine CTL. Mice were immunized with a recombinant vaccinia virus expressing the HCV NS5 gene, and the primed spleen cells were restimulated in vitro with peptides. CTL from $H-2^d$ mice responded to a single 16-residue synthetic peptide which is identified herein as "P17" and which corresponds to residues 2422–2437 of the HCV open reading frame. This relatively conserved epitope was presented by $H-2^d$ class I major histocompatibility complex (MHC) molecules to conventional CD4$^-$CD8$^+$ CTL, but was not seen by CTL restricted by $H-2^b$. Moreover, exon-shuffle experiments using several transfectants expressing recombinant $D^d/L^d$ and $K^d$ demonstrated that this peptide is seen in association with α1 and α2 domains of the $D^d$ class I MHC molecule.

The amino acid sequence of the P17 peptide differs by one residue from homologous segments of this nonstructural region from three other HCV isolates. Variant peptides with single amino acid substitutions were made to test the effect of each residue on the ability to sensitize targets. Neither substitution affected recognition. Therefore, these conservative mutations affected peptide interaction neither with the $D^d$ class I MHC molecule nor with the T cell receptor.

Murine CTL cross-react with peptides representing all four sequenced HCV isolates from the USA and Japan. If human CTL display similar crossreactivity, therefore, then the peptides of this invention should be valuable for HCV diagnosis and vaccine development. Thus, the peptides of this invention would be candidates for components of an HCV vaccine to prevent or treat the virus infection. In addition, these peptides would be useful for development of diagnostic or prognostic methods based on determining whether the cellular immune system evidences a response to the NS5 protein of HCV.

Details of the peptides and other aspects of this invention are presented below.

A. Definitions

The following definitions are provided for some of the terms used throughout this specification.

Amino Acid Residues—identified herein are in the natural L-configuration. The following abbreviations for amino acid residues are used:

| SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine, |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

All amino acid sequences are represented herein by formulae with left-to-right orientation in the conventional direction of amino-terminus to carboxy-terminus.

Peptide—is used herein to designate a linear series of amino acid residues connected one to the other by peptide bonds between the α-amino and carboxy groups of adjacent residues. Peptide, as used herein, does not encompass a naturally occurring protein such as the NS5 protein of HCV.

Antibody—in its various grammatical forms is used herein as a collective noun that refers to a population of immunoglobulin molecules or immunologically active portions of immunoglobulin molecules, i.e., molecules that contain an "antigen binding site" or paratope. An antigen binding site is that structural portion of an antibody molecule that specifically binds to an antigen at a B cell epitope.

B. The Peptides

To construct a peptide displaying a T cell epitope which induces in lymphocytes of a mammal a cytotoxic T cell response against cells which express a particular protein, it is necessary to test empirically a series of peptides comprising candidate T cell epitopes. Such candidates are identified by amphipathic scores (35) which indicate the tendency of an amino acid sequence to form a amphipathic helix. The correlation between class II-restricted T-cell epitopes and regions with amphipathic scores >4 remains highly statistically significant even as evaluated on 92 epitopes known in 1991 (12,13) (p<0.0003), and is significant on a smaller set of CTL epitopes studied as well. But, a correlation between the magnitude of the score above this threshold and the probability that a site will be recognized by T cells has not been found.

By the above approach it has been discovered that a peptide having an amino acid sequence selected from the group consisting of MSYSWTGALVTPCAAE [SEQ ID NO: 1], MSYTWTGALVTPCAAE [SEQ ID NO: 2] and MSYTWTGALITPCAAE [SEQ ID NO: 3] induces a cytotoxic T cell response in mammalian lymphocytes against cells expressing hepatitis C virus NS5 protein. Therefore, a peptide can be synthesized, in accordance with the presence invention, which displays a T cell epitope that induces a cytotoxic T cell response in lymphocytes of a mammal against cells expressing hepatitis C virus NS5 protein. A peptide of the present invention can comprise all or a portion of an exemplary amino acid sequence recited above, or an immunological equivalent of an exemplary sequence. In particular, a peptide of this invention can comprise sequences of amino acid residues 2422–2437 of an HCV polyprotein, which residues are contained in the NS5 region of the HCV polyprotein, or immunological equivalents of amino acid residues 2422–2437 of an HCV polyprotein.

The phrase "immunological equivalent" relates to the fact that certain amino acid substitutions or deletions may be made in an immunogenic peptide having a natural amino acid sequence of residues 2422–2437 of an HCV polyprotein, and yet the resulting peptide will provoke an immune response that is substantially equivalent to that of the original immunogenic peptide. Such substitutions or deletions can be made in accordance with established principles, some of which are discussed below.

In this regard, peptides having the ability to induce a cytotoxic T cell response against cells expressing residues 2422–2437 of an HCV polyprotein are considered immunologically equivalent to the peptide of this invention. More particularly, to be immunologically equivalent to residues 2422–2437 of an HCV polyprotein, a peptide must be (1) presentable by a target cell having an MHC molecule that presents the subject portion of an HCV NS5 protein and (2) be recognizable in the context of that MHC molecule by cytotoxic T lymphocytes that have been primed with NS5 protein of hepatitis C virus.

To be an "immunological equivalent", therefore, it is not necessary that each residue of the natural HCV epitope sequence or fragment thereof be replaced with an immunologically equivalent residue, but rather that the peptide as a whole evoke a substantially equivalent immune response. Thus, substitutions of one amino acid for another, either conservative or non-conservative, where such changes provide certain advantages in their use, are contemplated in the practice of this invention. Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. Conservative substitutions also include the use of a substituted amino acid in place of an unsubstituted parent amino acid provided that such a peptide also displays the requisite binding activity.

Systematic methods for determining which residues of a linear amino acid sequence are required for binding to a specific MHC protein are known. See, for instance, Allen, P. M., et al., *Nature* 327:713–717 (1987); Sette, A. et al., *Nature* 328:395–399 (1987); Takahashi, H. et al., *J. Exp. Med.* 170:2023–2035 (1989); Maryanski, J. L., et al., *Cell* 60:63–72 (1990).

Similarly, systematic methods for determining which residues of a linear amino acid sequence are required for binding a specific antibody are known, and essentially the same methods may be applied to determine which residues of a sequence are required for recognition by a T cell receptor. See, for instance, PCT Application WO 8403564 on "Determination of amino acid sequence antigenicity for location of active sequence in a protein" by H. M. Geysen, the entire disclosure of which is incorporated herein by reference. This application discloses a method for determining an amino acid sequence antigenically active within a known amino acid sequence of a protein or part of it which comprises (1) synthesizing peptides having overlapping amino acid sequences, each comprising a sequence corresponding to a sequence within the known amino acid sequence; (2) contacting the peptides with antibody against the protein or portion of interest; and (3) detecting or determining the presence or absence of antigen-antibody reaction between each peptide and antibody to indicate whether the peptide has antigenic activity.

Application of this approach to identifying immunological equivalents of the sequence of the peptide of this invention, exemplified by a peptide comprising residues 2422–2437 of the Chiron HCV1 polyprotein sequence, requires substitution of a cytotoxic T cell specific for target cells expressing an HCV NS5 protein in place of the antibody against the protein of interest. Suitable cytotoxic T cells for this purpose include, for instance, lymphocytes from a mammal that has been infected with HCV or immunized with a recombinant vaccinia virus expressing an HCV NS5 protein, or cytotoxic T cell clones derived from such immunocytes by repeated stimulation with a peptide of this invention, as described below in Example 2. The cytotoxic T cell can be used for identifying immunological equivalents of an exemplary peptide of this invention by further defining those residues within the exemplary sequence which are required for presentation of a functional T cell epitope of the HCV NS5 protein, according the above method of Geysen as modified by substituting T cells for an antibody, for instance, or as described by Takahashi, H. et al., *J. Exp. Med.* 170:2023–2035 (1989a), *Science* 246:118–121 (1989b), and *Science* 255:333–336 (1992).

Application of the above-described methods is expected to identify a linear subset of the sequence of residues 2422–2437 of an HCV polyprotein protein that are required for T cell epitope activity according to this invention. It is known that a functional T cell epitope, capable of being presented by an MHC molecule and of being recognized by a T cell receptor, usually comprises a linear sequence of nine amino acids, although some linear epitopes consisting of eight or ten amino acids are known. See, for instance, Falk, K. et al., *Nature* 351:290 (1991); Jardetzky, T. F., et al., *Nature* 353:326–329 (1991); Hunt, D. F., et al., *Science* 255:1261–1263 (1992); and Romero, P., et al., *J. Exp. Med.* 174:603–612 (1991).

Therefore, a sequence which is immunologically equivalent to the sequence of an exemplary peptide of the present invention is believed to require at least eight amino acids, for instance, eight consecutive residues of an exemplary 16 amino acid sequence which are shown to be required for T cell epitope function as described above. However, a peptide of less than eight amino acids, of seven or six amino acids, for instance, possibly could be found to be immunologically equivalent to an exemplary peptide of this invention by the methods described above, and such a peptide still would be within the scope of the present invention. In short, the peptide of this invention comprises at least about eight amino acids, which includes as few as six amino acids.

Beyond the minimum number of residues required for a functional T cell epitope, the length of the peptide of this invention can vary, for example, depending on the type of carrier used for immunization. It is generally preferred that the peptide be of a length which minimizes the number of epitopes other than the desired epitope so that the chances of interference between epitopes is minimized. Moreover, when preparing peptides by chemical synthesis, additional residues will generally lengthen the time and cost required for their preparation, and reduce the purity and yield of final product. Thus, synthetic peptides of less than 50 residues are preferred, and less than 30 residues are more preferred. Peptides which present epitopes in addition to that of the HCV P17 epitope, however, certainly also are within the scope of the present invention. Routine experimentation will yield the optimum length(s) for such peptides.

Examples of peptides which provide the objects of this invention include a 16-residue peptide that displays a T cell epitope which induces a cytotoxic T cell response in lymphocytes of a mammal against cells expressing hepatitis C virus NS5 protein, having the following sequence of amino acids: [SEQ ID NO: 2] MSYTWTGALVTPCAAE. This sequence was derived from residues 2422–2437 of the NS5 protein of an HCV isolate obtained by the U.S. FDA and, therefore, has been designated "P17FDA". The P17FDA sequence differs in one residue from the corresponding NS5 sequence of another U.S. isolate, the Chiron HCV1 sequence [SEQ ID NO: 1] MSYSWTGALVTPCAAE (26), designated P17. The P17FDA sequence also differs by another single residue from a sequence which is conserved at this site in two independent Japanese isolates [SEQ ID NO: 3] MSYTWTGALITPCAAE (29,60), designated P17JPN. Thus, the peptides designated P17, P17FDA and P17JPN represent three natural variants of the portion of the HCV NS5 protein corresponding to residues 2422–2437 of the Chiron HCV1 polyprotein, each of which displays an epitope that induces a cytotoxic T cell response in lymphocytes of a mammal against cells expressing hepatitis C virus NS5 protein.

Additional peptides of this invention can comprise natural sequences of portions of NS5 proteins of other isolates of HCV which correspond to the P17 sequence of the Chiron HCV1 isolate. Such additional natural NS5 sequences may be determined as taught in below in Example 2. Thus, HCV viral RNA is extracted from infected tissue (19). The RNA is reverse transcribed and amplified by the polymerase chain reaction using specific HCV primers as previously described (9). Then the PCR product is ligated into a cloning vector suitable for amplification and sequencing of the NS5 DNA.

It is known in the art that the polyproteins from different isolates of HCV may comprise more or less than the 3011 amino acids of the Chiron HCV1 isolate. For instance, the polyproteins of the Japanese isolates comprising the sequence designated P17JPN consist of only 3010 residues, of which the P17JPN sequence comprises residues 2421–2436. Therefore, to find sequences which correspond structurally to the P17 sequence of this invention (residues 2422–2437 of the Chiron HCV1 sequence), newly determined NS5 sequences are aligned with homologous portions of known NS5 sequences, for instance, the Chiron HCV1 sequence, to identify those residues of the new sequence which correspond to residues 2422–2437 of the known HCV polyprotein. Peptides having sequences corresponding to the P17 sequence, as determined from analysis of the cloned PCR product, are then made and tested for T cell epitope function as described below in Example 2.

The methods cited above can serve not only to identify residues in the linear sequence of an NS5 protein which are required for T cell epitope activity, but also to define the permissible range of substitutions of amino acids in those positions which are required for displaying the T cell epitope. Thus, in addition to natural HCV NS5 amino acid sequences, other amino acid sequences may be included in a peptide of this invention to present substantially the same functional epitope of the HCV NS5 protein. These non-natural amino acid sequences may be identified by substituting various amino acids for those in a natural sequence of residues of NS5 which are required for T cell epitope function and testing the resulting sequences for retention of such function as in Example 2.

For example, PCT Application WO 8606487 discloses a method for developing "mimotopes" which mimic an epitope on a protein, for instance. See also, document (71). This method involves detecting or determining the sequence of monomers which is a topographical equivalent of a ligand (e.g., epitope) which is complementary to a particular receptor of interest (e.g., an antibody). The method comprises (a) synthesizing catamers of formula D2–D1, wherein D1=a designated monomer (such as a natural L-amino acid or a synthetic D-form or otherwise modified amino acid) selected from a first set of monomers and D2=a designated monomer selected from a second set of monomers which may be the same as the first set. These catamers comprise catamers in which each designated monomer is systemically varied to contain members from the respective set of monomers. The method further comprises (b) contacting each catamer with the receptor of interest and (c) detecting or determining the presence or absence of binding between each catamer and the receptor. The aforementioned PCT Application No. WO 8600991 and document (71) disclose further details of identifying amino acid sequences topologically equivalent to an epitope (i.e., a mimotope) by testing catamers of partially defined structure for antibody binding.

Hence, by use of cytotoxic T lymphocytes and their receptors, according to this invention, and the methods for developing mimotopes described above, one skilled in the art may develop a peptide of this invention, which presents an epitope that is immunologically equivalent to the HCV NS5 T cell epitope presented by the exemplary peptides disclosed herein. The mimotopes of these immunologically equivalent "peptides" need not contain any natural amino sequence of HCV, or, in fact any natural amino acids at all.

A peptide in accordance with this invention which has a sequence that is partly identical to the natural sequence of the T cell epitope of HCV NS5 (because one or more conservative or nonconservative substitutions or deletions have been made) usually but not necessarily will have substituted or deleted no more than about 30 number percent, advantageously no more than about 20 number percent, and preferably no more than about 10 number percent of the amino acid residues which comprise all or part of a NS5 T cell epitope, except where additional residues have been added at either terminus, for instance to provide a "linker" by which the peptides of this invention can be conveniently affixed to another substance, such as a label, a solid matrix, or a carrier.

In addition, the amino acid sequence of a peptide in accordance with this invention can differ from the natural sequence of the HCV NS5 epitope by the sequence being modified by terminal-$NH_2$ acylation, e.g., acetylation. Such acylation is used to reduce the charge on the synthetic peptide, according to principles well known in the art.

A peptide in accordance with this invention can be synthesized by any of the techniques that are known to those skilled in the peptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward & J. D. Young, SOLID PHASE PEPTIDE SYNTHESIS, W.H. Freeman Co., San Francisco, (1969); M. Bodanszky et al., PEPTIDE SYNTHESIS, John Wiley & Sons, Second Edition, (1976); and J. Meienhofer, HORMONAL PROTEINS AND PEPTIDES, Vol. 2, p. 46, Academic Press, New York (1983) for solid phase peptide synthesis, and E. Schroder & K. Kubke, 1 THE PEPTIDES, Academic Press, New York (1965) for classical solution synthesis, the entire disclosure of each being hereby incorporated herein by reference. Appropriate protective groups usable in such synthesis are described in the above texts and in J. F. W. McOmie, PROTECTIVE GROUPS IN ORGANIC CHEMISTRY, Plenum Press, New York (1973), the entire disclosure of which is also incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively-removable protecting group. A different, selectively-removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final peptide.

Simplified methods for solid phase synthesis of peptides on a small scale also are known. See for instance, Houghten, R. A., *Proc. Natl. Acad. Sci. U.S.A.* 82:5131–5135 (1985); and Houghton, M., Q. -L. Choo, & G. Kuo, European Patent Application 88310922 (1988).

C. Assays and Diagnostic Methods

The present invention contemplates various assay methods for detecting in lymphocytes of a mammal cytotoxic T cells that respond to a T cell epitope of NS5 protein of hepatitis C virus.

In a preferred embodiment, this assay comprises a first step (a) of contacting target cells with a peptide of this invention. Preferably, these target cells are known to be MHC-compatible with lymphocytes which are to be tested for the HCV-specific cytotoxic T cells. A second step (b) requires incubating the lymphocytes to be tested for said cytotoxic T cells with a peptide of this invention, under in vitro conditions sufficient to restimulate the HSV NS5-specific CTL to respond to appropriate target cells. A third step (c) requires determining whether the tested lymphocytes exert a cytotoxic effect on the target cells, thereby indicating the presence of CTL that recognize a T-cell epitope of NS5 protein of hepatitis C virus.

While exemplary assay methods are described herein using murine lymphocytes, the invention is not so limited. For example, the present invention contemplates detection of human CTL, for instance in blood or other tissues of patients known or suspected to be infected with HCV, by appropriately adapting methods known for detecting other human CTL. See, for instance, Clerici, M., et al., *J. Imm.* 146:2214–2219 (1991).

The assay of this invention is useful for determining whether the immune system of a mammal has been provoked by the NS5 protein of HCV, thereby to determine whether the occurrence and magnitude of such a response can be correlated with either the occurrence of HCV infection (i.e., for diagnosis) or the severity of the pathogenic effect of the virus (i.e., as a prognostic indicator).

D. Vaccine and Therapeutic Compositions

The peptides of this invention are thought to have utility for a vaccine to prevent HCV infection or for therapeutic purposes in individuals infected with HCV. For example, the peptides can be used by themselves, or they can be used to prepare immunogenic conjugates in which a peptide is conjugated to an agent which provokes an immune response to a complex comprising the conjugated peptide bound to a carrier protein, according to methods known in the art. See, for instance, M. F. Good, *Science* 235:1059–1062 (1987); and Palker, T. J., *J. Imm.* 142:3612–3619 (1989). Agents which can be conjugated to peptides to provoke an immune response include toxoids such as diphtheria toxoid or tetanus toxoids, which are commonly recognized by the body (of immunized persons) and eliminated by the immune system. Alternatively, a gene sequence encoding the peptide may be incorporated into a recombinant gene and expressed as part of a vector, for instance, a recombinant virus such as vaccinia virus made by the method of Chakrabarti, S., et al., *Nature* 320:535–537 (1986).

The peptide of the present invention also may be incorporated into a larger peptide comprising additional epitopes, either other T cell epitopes or B cell epitopes. Thus, the peptide may be used as part of a multivalent vaccine which induces cytotoxic T cell responses to multiple epitopes of HCV or of HCV and another virus. In addition, the multivalent vaccine peptide may include helper T cell epitopes and B cell epitopes of HCV or another virus, to effect induction of an antibody response as well as a cytotoxic T cell response.

For instance, one could attach a helper T cell epitope from HIV, such as those described in Cease K. B., et al., *Proc. Natl. Acad. Sci. USA* 84:4249–4253 (1987), to provide T cell help for the CTL response. Also see Berzofsky, J. A., et al., *J. Clin. Invest.* 88:876–884 (1991); for peptides generating antiviral cytotoxic T lymphocytes, Hart, M. K., et al., *Proc Natl Acad Sci USA* 88:9448–9452 (1991); and for peptides inducing an antibody response, Hart M., K., et al., *J. Immunol.* 145:2677–2685 (1990).

Those skilled in the art of preparing pharmaceutical compositions will realize how to prepare the peptides and conjugates described above for pharmaceutical use in composition comprising accepted pharmaceutical carriers.

Rationale for a vaccine. HCV is probably a member of the Flaviviridae family which includes both the classic flaviviruses such as yellow fever virus and the pestiviruses of animals such as bovine viral diarrhea virus (11). The classic flaviviruses have arthropod vectors and cause only acute disease. The pestiviruses, on the other hand, have no known arthropod vectors and may cause chronic infections as well as acute disease. HCV causes acute, self limited infections, but like pestiviruses, it also commonly causes chronic infections and liver diseases that includes chronic active hepatitis, cirrhosis, and probably hepatocellular carcinoma. The mechanism of chronicity and the pathogenesis of the chronic liver disease is not understood. It does not seem likely that the chronic virus infection is directly cytopathic as it would result in much greater liver destruction. Therefore, as in hepatitis B infections, an immune mechanism has been proposed.

Neutralizing antibodies to most flaviviruses are directed against epitopes in the envelope glycoportein. Either such antibodies are not commonly made by people infected with HCV, or there is not yet available an assay able to detect them. Results of sequence analysis of the two putative envelope glycoproteins of HCV has revealed considerable strain variability (23,27,67) which may further confound attempts to produce an antigen that induces neutralizing antibodies of broad reactivity.

More particularly, recent reports of HCV sequence diversity allow comparison of several isolates (9,23,37,44,67), reviewed in (27). It is noteworthy that C, NS3, NS4, and NS5 regions of HCV exhibit greater sequence conservation in contrast to the hypervariability of the putative envelope glycoproteins encoded by the E1 and E2/NS1 genes and the greater heterogeneity of NS2. This hypervariability of the HCV envelope protein suggests that this region may be under selective pressure for variation of a protective B cell or T cell epitope, as suggested in the case of the HIV-1 envelope protein V3 loop, which is the principal neutralizing domain as well as an immunodominant determinant for CTL in both the human and the mouse (10,21,46,53,57).

The hypervariability suggests an ability of this virus to escape the immune system by rapid mutation. Within the groups of isolates, broadly subdivided by comparison of all the reported HCV sequences, NS5 shows 95% to 100% homology (27). The variability is also relevant to the issue of multiple infection with different HCV isolates. Most recent sequence analysis of HBV genome from fulminant hepatitis suggested that naturally occurring viral mutations may predispose the infected host to more severe liver injury (34,45). Accordingly, cross-neutralization of variants by antibody and cross-recognition of variants by T cells are important issues in the development of vaccines to prevent the rise of escape mutants from the immune system.

For these reasons, the present inventors undertook studies to enable determination of whether T cell epitopes of HCV are important in pathogenesis or protection from infection, particularly T cell epitopes displayed by the relatively conserved NS5 protein. Previous studies have shown that $CD8^+$ CTL recognize hepatocytes from patients with chronic NANB hepatitis in a non-MHC restricted manner (28). It had been thought that CTL against virus-infected cells most often recognize the nucleoprotein of the virus expressed on the infected cells and lyse the cells (52). In hepatitis B infection, for instance, CTL are thought to be responsible for the pathogenesis of chronic type B hepatitis and to lyse hepatitis B-virus-infected hepatocytes by recognizing the viral antigen expressed in the infected cells (39,42).

Class I and class II MHC molecules allow T cells to recognize polypeptide fragments of proteins following processing of foreign antigens (4,51,55,61,70). Therefore, it should be feasible to develop peptides that display T cell epitopes similar to those present on fragments of proteins following processing. Synthetic peptide vaccines comprising such epitopes may elicit fewer deleterious immune responses than the whole protein or attenuated or killed virus (5).

The experimental results disclosed herein, based on studies using mice as a model for the human immune system, indicate that CTL may recognize the product of the probably HCV RNA polymerase gene, a nonstructural region, on cells infected with the virus in association with class I MHC molecules. Because murine cells cannot be infected with HCV, this proposition cannot be tested directly in HCV-infected mice.

Nevertheless, the present results show a reasonable basis for expecting that the peptide of this invention will induce an in vivo cytotoxic T cell response against HCV NS5-infected cells in a mammal. Thus, the peptide has produced murine CTL lines with ability to kill syngeneic target cells expressing the HCV NS5 as well as target cells pulsed with peptide P17 (HCV residues 2422–2437 within NS5).

The peptide induced a CTL response lymphocytes of $H-2^d$ mice, but not of $H-2^b$ mice, indicating that $H-2^d$ is an immune response (Ir) gene responder haplotype to P17 whereas $H-2^b$ is not a responder. Further, the response to P17 of HCV NS5 depends on both the α1 and α2 domains of the $D^d$ class I molecules, as shown by responses of eight L cell ($H-2^k$) transfectants with different exon shuffles between $D^d$ and $L^d$. Similar results were obtained for effective presentation of the peptides, P18 (58) and HP53, from HIV-1 gp160 (56). In the context of vaccine development, it is of interest that P17 and the HIV-1 gp160 peptides P18 and HP53, which were all presented by the same $D^d$ class I MHC molecule, share no striking similarity in sequences except similarity in amphipathic hydrophobicity profiles when each is folded as a short highly amphipathic alpha helix. Although insufficient homology is present to define an obvious motif for $D^d$ binding, analysis of residues involved in $D^d$ binding (58) for each peptide should shed light on the structural requirements for the $D^d$ specificity.

To get the maximal lysis, the peptide concentration required to stimulate CTL in vitro secondarily or to sensitize targets appeared to be very low (0.1–1 $\mu$M) for P17. This result indicates that P17 binds with a relatively high affinity to class I MHC molecules in $H-2^d$, which is an important characteristic of a peptide immunogen from a practical point of view, for instance, in minimizing cost per dosage. Also, P17 did not show any toxicity that might affect its activity in CTL stimulation or utility in vivo.

Availability of three different sequences of HCV variants (USA and Japan) of this relatively conserved epitope (26, 29,60) permitted synthesis of two variant peptides of this invention, each differing at one or two residues from the P17 sequence of the Chiron isolate (26), in order to define the effect of naturally occurring viral mutation on the peptide presentation by the $D^d$ molecule and CTL recognition. The single amino acid substitution at position 2424 (T→S) and at position 2431 (V→I) did not reduce the CTL recognition of peptide P17 in BALB/c mice. Therefore, these point mutations at which all four cloned HCV isolates from USA and Japan differ seem to affect peptide interaction with neither the $D^d$ class I MHC molecule nor the T-cell receptor. If human CTL display similar crossreactivity for this site, this peptide may be useful as a CTL epitope for vaccine development despite the few conservative substitutions found in nature.

As to the expected effectiveness of such a vaccine, there are many lines of evidence that CTL can block outgrowth of virus in cells which have been previously infected (17,28, 39,42,47,48,63,66). Likewise, it is thought that a vaccine eliciting HCV-specific CTL may be protective against HCV. In the present work, P17 from HCV NS5 region was presented by class I MHC molecules to $CD8^+CD4^-$ CTL. The high conservation and cross-reactivity of peptide P17 suggests that this peptide could play a role as a component of a broadly effective vaccine for HCV, if also seen by human CTL.

In previous work with HIV-1 proteins gp160 and reverse transcriptase, epitopes seen by murine CTL were also seen by human CTL (10,24,57). T-cell proliferation but not cytotoxicity has been observed in response to P17 stimulation in one chronically infected chimpanzee. This primate is the only confirmed animal model for hepatitis caused by HCV.

Whether the P17 site is presented by a diversity of human class I MHC alleles and whether P17 is also presented by class II MHC molecules to $CD4^+$ CTL will be determined according to methods known in the art. See, for instance, Clerici, M. J., Imm 146:2214–2219 (1991); Clerici et al., Nature 339:383–385 (1989). This information will be useful, not only for vaccine development but also for analysis of the versatility of viral peptides for binding MHC molecules. Identification of critical amino acids in the peptide for binding to MHC and T-cell receptor may yield new information on the molecular basis of escape mutation by HCV and chronicity of HCV infection as well.

The following examples are provided solely for illustrative purposes, and do not in any manner limit this invention.

EXAMPLE 1

Design and Synthesis of Peptides Comprising Candidate T Cell Epitopes of Hepatitis C Virus NS5 Protein Peptide design. Based on the sequence of the NS5 region of an isolate of HCV, which has been published by workers at Chiron Corporation (26), hereinafter the "Chiron HCV1 sequence," a series of 28 peptides was synthesized, including some overlapping peptides, covering much of the HCV putative RNA polymerase sequence encoded by the NS5-like region. The peptide sequences were selected on the basis of amphiphathicity (12,13,15,35) as potential T-cell epitopes.

Subsequent sequencing of the whole NS5 region of the HCV isolated in the FDA used to construct the recombinant vaccinia virus showed that 13 out of 28 peptides had mutations in up to 3 residues compared to the published Chiron HCV1 sequence (FIG. 1A, SEQ ID NOS. 8, 9, 10, 14, 15, 20, 21, 23, 26, 27, 28 and 31).

Peptide Synthesis and Purification. HCV NS5 peptides were prepared by the simultaneous multiple peptide method of solid-phase peptide synthesis, in polypropylene mesh "tea-bags" as described (25). Peptides were desalted by reverse-phase chromatography on C18 Sep-Pak columns (Waters Associates, Milford, Mass.), and analyzed by HPLC. Some peptides were prepared by an automated peptide synthesizer (model 430A; Applied Biosystems, Inc., Foster City, Calif.) using t-Boc chemistry and purified by HPLC. Peptide HIV P18 was prepared under GMP conditions by Peninsula Labs (Belmont, Calif.).

EXAMPLE 2

Identification of a Peptide that Induces a Cytotoxic T Cell Response against Cells Expressing Hepatitis C Virus NS5 Protein Overview. To identify a possible T cell epitope of hepatitis C virus NS5 protein, the peptides of Example 1 were tested in BALB/c and BALB.B mice for their capacity to generate CTL specific for the HCV NS5 region. The spleen cells of mice immunized 4 weeks earlier with the NS5-expressing recombinant vaccinia virus (vHCV) ($10^7$ PFU i.v.) were stimulated in vitro with 4 $\mu$M peptides, in the presence of IL-2 (medium containing 10% supernatant of cultured rat lymphocytes stimulated with Con A).

BALB/c mice that were immunized with vHCV developed CTL responses to peptide P17 but not to any of the other peptides (FIG. 1B). Because no antibodies specific for the HCV region cloned into vaccinia were available, there is no direct evidence for expression of protein sequences to the carboxy-terminal side of P17. Although there is no evidence that such sequences are not expressed, it remains possible that lack of expression of sequences carboxy-terminal to P17 could account for the lack of response to the peptides following P17.

It is also possible that negative responses were due to differences in 11 of the peptides between their sequences based on the published sequence and the sequence of the isolate of HCV cloned into vaccinia. Because these and other reasons could account for negative responses, only positive responses are significant in the context of determining whether a particular portion of the NS5 protein contains a T cell epitope that can induce a CTL response to the NS5 protein.

BALB.B (H-$2^b$) mice showed no response to any peptide tested. However, a recombinant vaccinia virus cannot be used to stimulate spleen cells from mice immunized with that recombinant without activating a vaccinia virus-specific response that overwhelms the response to the inserted gene product when vaccinia-infected targets are used. Therefore, BALB.B cells infected with vHCV expressing the whole NS5 protein cannot be used to determine whether BALB.B mice might respond to other epitopes of HCV not tested with the present peptides.

Mice. BALB/c mice were purchased from Charles River Laboratories and BALB.B mice were bred in our own colony from breeders kindly provided by Dr. F. Lilly (Albert Einstein College of Medicine, New York). Mice used were 8 weeks old.

Recombinant Vaccinia Viruses Expressing NS5 Protein. The region of the HCV genome coding for amino acids 1959 through 2872, representing most of the predicted NS5 region based on analogy to flaviviruses, was cloned into vaccinia virus under the P7.5 promoter as described by Chakrabarti et al. (7). The resulting recombinant vaccinia virus was designated vHCV#3. HCV viral RNA was extracted from the liver biopsy of a chimpanzee acutely infected with the H strain of HCV (FDA isolate of the HCV/H (19). The RNA was reverse transcribed and amplified by the polymerase chain reaction using specific HCV primers as previously described (9). The 5' primer included an ATG sequence at its 5' end. This PCR product was ligated into the StuI site of the pSC11ss transfer vector and then inserted into vaccinia virus by homologous recombination. The vaccinia was amplified in BS-C-1 cells and used for immunizing the mice to generate HCV NS5-specific CTL.

vSC8 (recombinant vaccinia virus containing the *Escherichia coli* lacz gene), and vSC25 (recombinant vaccinia virus expressing the HIV-1 IIIB gp160 envelope glycoprotein without other structural or regulatory proteins of HIV), obtained from Dr. Bernard Moss, NIAID, NIH, have been described (7) and were used as a control vaccinia for immunizing the mice.

CTL Generation. Mice were immunized intravenously with $10^7$ PFU of recombinant vaccinia virus. 4–6 wk later, immune spleen cells ($5\times10^6$/ml in 24-well culture plates in complete T cell medium (CTM; 1:1 mixture of RPMI 1640 and EHAA medium containing 10% FCS, 2 mM L-glutamine, 100 U/ml penicillin, 100 $\mu$g/ml streptomycin and $5\times10^{-5}$ M 2-ME) were restimulated for 6d in vitro with peptides and 10% Con A supernatant-containing medium (rat T cell Monoclone; Collaborative Research, Inc., Bedford, Mass.).

Lymphocytes were restimulated with peptides rather than with the recombinant vaccinia virus used for immunization, because experience with other antigens showed that restimulation of recombinant vaccinia-immune spleen cells with recombinant vaccinia virus leads to a predominant response to the vaccinia and difficulty detecting weaker CTL responses to peptides from the inserted recombinant gene. However, this problem did not occur with P17, as shown in Table 1 (below).

Logistically, it was not practical to perform an experiment in which all 28 peptides were used to stimulate individual effector populations. Therefore, mixtures of three peptides each (at 4 μM) were used to stimulate separate populations of lymphocytes. Each resulting population of effector cells was tested against the three peptides in the corresponding mixture individually. However, stimulation with a mixture of all candidate T cell epitope peptides was avoided to prevent missing sites that might compete with each other for binding to MHC (20).

Experience has shown that the frequency of peptides binding to a given class I molecule is low enough, and the frequency of finding a peptide that can compete at a concentration as low as 4 μM is sufficiently low, that it would be unlikely that a positive response was missed because of competition between two peptides in a mixture of three at 4 μM. Nevertheless, such competition cannot be formally excluded as one of many possible reasons for negative results with some of the peptides.

Long-term CTL lines were also generated by repetitive stimulation of immune cells in medium containing rat IL-2 with a combination of 0.5–1 μM peptide and syngeneic spleen cells ($2.5 \times 10^6$ cells/ml) that had been pulsed with peptides at 10 μM for 4 h and then irradiated.

CTL Assay. Cytolytic activity of in vitro secondary CTL or CTL lines was measured as previously described (57,62) using a 6-hour assay with $^{51}$Cr-labelled targets. For testing peptide specificity of CTL, effectors and $^{51}$Cr-labeled targets were mixed with various concentrations of peptide, or effectors were cocultured with peptide-pulsed targets. The percent specific $^{51}$Cr release was calculated as 100× [(experimental release-spontaneous release)/(maximum release-spontaneous release)]. Maximum release was determined from supernatants of cells that were lysed by addition of 5% Triton-X 100. Spontaneous release was determined from targets cells incubated without added effector cells. The 18Neo (H-$2^d$; class I MHC$^+$, class II MHC neomycin-resistance gene transfected 3T3 fibroblast (57), L cell (L28; H-$2^k$), and EL4 thymoma cell (H-$2^b$) were used as targets.

EXAMPLE 3

Specificity of the T Cell Epitope that Induces a Cytotoxic T Cell Response against Cells Expressing Hepatitis C Virus NS5 Protein Identification of the class of NEC molecule that presents peptide 17. Because class II-negative fibroblast targets were used to detect CTL, and lysis was restricted under MHC-linked control, P17 probably was presented by class I MHC molecules to CTL in the lymphocytes taken from H-$2^d$ mice immunized with vaccinia virus expressing NS5 protein. The failure of the BALB.B (H-$2^b$) mice to respond to any peptide tested suggests that H-$2^b$ class I MHC molecules cannot present this peptide.

Cross-reactivity of natural sequence variants of the NS5 T cell epitope. The FDA isolate (SEQ ID NO: 2) of HCV used to make the vaccinia recombinant vHCV was found to differ in the P17 sequence (SEQ ID NO: 1) from the Chiron HCV1 sequence (26) by one residue, and from a Japanese sequence (SEQ ID NO: 3) which was conserved at this site in two independent Japanese isolates (29,60), by another single residue (FIG. 1A and SEQ ID NOS. 1–3). Because mice were immunized with vHCV expressing the FDA sequence but the CTL were restimulated with and tested on targets pulsed with the P17 peptide made according to the Chiron sequence, the CTL were expected to crossreact with these two variants of HCV.

To demonstrate this cross-reactivity directly, two variant P17 peptides were prepared, with amino acid substitutions at positions 2425 and/or 2431, corresponding to the FDA (P17FDA, SEQ ID NO: 2) and Japanese isolates (P17JPN, SEQ ID NO: 3) (FIG. 1A and SEQ ID NOS: 2 and 3). Responses to such variant peptides, differing at one or two residues, would define the effect of naturally occurring viral mutation on peptide presentation by the H-$2^d$ class I MHC molecules and on recognition by the T cell receptor of the NS5-specific CTL.

Specificity of CTL for NS5 was demonstrated at the level of lymphocyte priming in vivo, restimulation in vitro, and expression on the target cells in the CTL assay (Table 1, below). Only the recombinant vaccinia virus expressing the NS5 gene (vHCV), but not the control vaccinia viruses (vSC8, vSC25), primed mice for development of CTL specific for P17 or P17 variants (Table 1, below).

TABLE 1

Priming and boosting requirements for CTL induction in H-$2^d$ mice

| | | % Specific lysis | | | | | | |
|---|---|---|---|---|---|---|---|---|
| Immunization | Restimulation | vHCV | vSCS | P17 | P17FDA | P17JPN | P18IIIB | unpulsed |
| none | P17 | 0.7 | 0.6 | 1.4 | | | | 0.5 |
| | P17FDA | 0.8 | 1.0 | | 2.9 | | | 2.8 |
| | P17JPN | 0.0 | 0.2 | | | 1.2 | | 3.2 |
| | vHCV | 0.1 | 0.2 | 1.3 | 0.4 | 2.0 | | 2.9 |
| vSC8 | P17 | 1.2 | 0.4 | 3.0 | | | | 0.3 |
| | P17FDA | 1.1 | 0.8 | | 2.3 | | | 3.2 |
| | P17JPN | 0.8 | 0.6 | | | 2.6 | | 0.6 |
| | vHCV | 41.6 | 37.1 | 0.9 | 0.3 | −0.1 | | 0.9 |
| | vSC8 | 47.6 | 44.5 | 2.8 | 0.5 | 1.9 | | 0.4 |
| vSC25 | P18IIIB | | | | 0.5 | 1.8 | 63.3 | 2.3 |
| | P17 | | | 0.8 | 0.1 | | 1.7 | 0.2 |
| | P17FDA | | | | 0.4 | | 1.7 | 0.3 |
| | P17JPN | | | | | 1.4 | 1.8 | 0.3 |
| | vHCV | 37.9 | 40.5 | −0.3 | 0.4 | 0.1 | 3.2 | 0.8 |
| vHCV | P17 | | 3.4 | 42.7 | 38.0 | 37.9 | 3.3 | 0.5 |
| | P17 1 μM | | 3.7 | 33.8 | 32.4 | 31.9 | 1.4 | 0.7 |
| | P17 0.1 μM | | 1.1 | 17.1 | 12.8 | 12.9 | 3.3 | 0.0 |
| | P17FDA | | 5.8 | 34.9 | 39.7 | 36.1 | 2.2 | 2.0 |
| | P17JPN | | 4.5 | 39.7 | 36.7 | 35.8 | 2.5 | 1.8 |

TABLE 1-continued

Priming and boosting requirements for CTL induction in H-2$^d$ mice

| | | % Specific lysis | | | | | | |
|---|---|---|---|---|---|---|---|---|
| Immunization | Restimulation | vHCV | vSCS | P17 | P17FDA | P17JPN | P18IIIB | unpulsed |
| | vHCV | 62.4 | 41.2 | 33.4 | 31.9 | 32.7 | 2.4 | 0.5 |
| | vSC8 | 48.1 | 41.7 | −1.1 | 1.6 | 0.0 | 2.2 | 0.5 |
| | P18IIIB | 2.2 | −0.8 | 1.8 | 0.8 | 1.6 | 1.6 | 0.5 |

More particularly, the ability of recombinant vaccinia viruses to prime and stimulate CTL specific for the products of inserted viral genes was used to generate CTL specific for HCV NS5 in BALB/c (H-2$^d$) mice. Non-immune or immune spleen cells were restimulated with P17 or P17 variants at 10 µM (or at concentrations indicated in Table 1; 0.1 or 1 µM of P17), P18IIIB at 0.1 µM, or vaccinia (vHCV, vSC8, or vSC25), and tested against vaccinia virus infected 18Neo, 18Neo pulsed with P18IIIB at 1 µM (an immunodominant CTL site, 315–329, of HIV-1 gp160 IIIB isolate) and unpulsed 18Neo in the presence of the P17, P17 variant peptides (10 µM), or no peptide at an E:T ratio of 100:1. Lysis in the absence of peptide was <4%. No toxicity of peptides against targets was observed. Spontaneous release was less than 20% of maximum release. Abbreviations in Table 1 are as follows: vHCV, recombinant vaccinia virus expressing NS5 of HCV; vSC8 and vSC25, control vaccinia virus and recombinant vaccinia virus expressing HIV-1 gp160, respectively; 18Neo, BALB/c 3T3 fibroblast, H-2$^d$.

Titration of peptide concentrations used for stimulation of immunized spleen cells demonstrated that lysis specific for P17 was induced at low concentration of peptide, 0.1 µM (Table 1). P17 required approximately 1–10 µM peptide for the stimulation of immune spleen cells to elicit the highest level of lysis against H-2-matched peptide-pulsed target cells. P17, P17FDA, and P17JPN were nearly interchangeable both for stimulation of CTL and for sensitization of targets (Table 1). Similar results were obtained in two independent experiments. Thus, complete crossreactivity between these variants was observed.

Long-term CTL lines specific for P17 and P17FDA were established by repetitive stimulation of spleen cells from vHCV-immunized mice with peptide-pulsed irradiated syngeneic spleen cells and IL-2 (Con A supernatant) (FIG. 2). The CTL lines stimulated with P17 or P17FDA (position 2425, S→T) manifested highly specific lysis of targets with each peptide, respectively. In the titration study, P17 and P17 variants sensitized target cells at similar levels for lysis by the CTL lines (between 0.01 and 10 µM; FIG. 2).

The extent of lysis reached a plateau in the presence of each peptide at concentrations above 0.1 µM. The maximum lysis achievable with P17 was comparable to the maximum lysis achievable with two other P17 variants at similar concentrations of peptide using the two different lines specific for P17 and P17FDA. Thus, these mutated residues did not affect the magnitude of response or concentration dependence, and the peptides were fully crossreactive. CTL stimulated in vitro with any of the three variants of the P17 peptide lysed targets in the presence of all three P17 variant peptides equally well (Table 1).

Therefore, conservative point mutations in the P17 sequence at which the four clones of HCV isolated in the USA and Japan differ did not affect either peptide interaction with H-2$^d$ class I MHC molecules or recognition by the T cell receptor.

Figure 3:
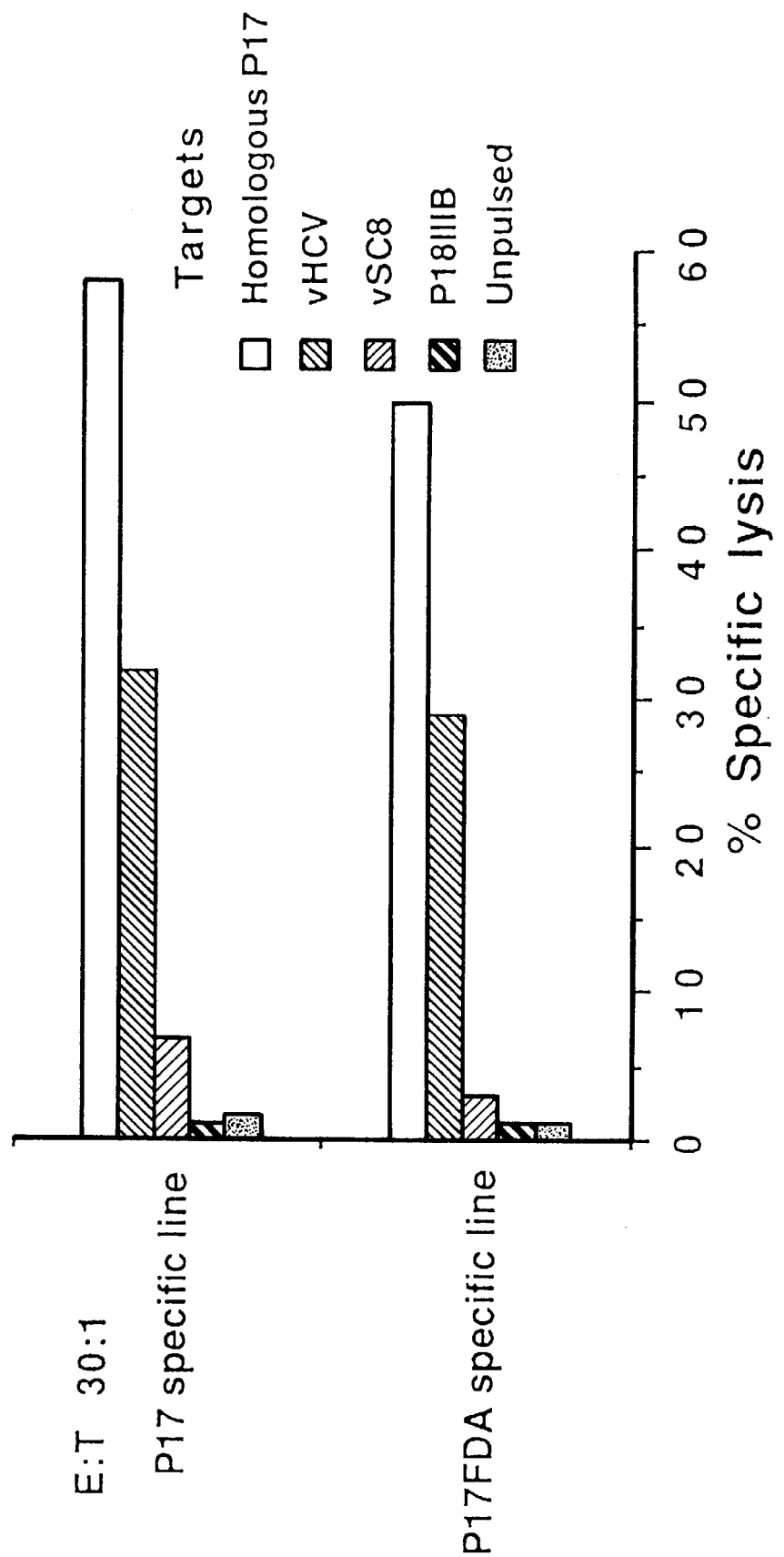
FIG. 3 shows results of testing of CTL lines specific for P17 and P17FDA restricted by H-$2^d$ for their cytotoxicity against the 18Neo cells (BALB/c 3T3 fibroblast) infected with vHCV vaccinia virus expressing NS5 (1 h, 37° C., multiplicity of infection 10:1, three washings before use) as well as 18Neo pulsed with each specific peptide (10 $\mu$M). As negative control targets, 18Neo (neo-gene transfected BALB/c 3T3) infected with control vSC8 vaccinia virus, P18IIIB (1 $\mu$M) pulsed, and unpulsed 18Neo were used. Standard errors of triplicates were generally <5% of the values, and comparable results were obtained in three independent experiments.

Recognition of processed NS5 protein by CTL induced with peptide. The CTL lines that were generated by repeated in vitro stimulation with peptide were shown to recognize target cells presenting the processed products of endogenously synthesized NS5 protein, not just the peptide. Thus, the CTL lines restricted by H-2$^d$ (BALB/c) were able to kill the vHCV-infected syngeneic target cells (18Neo cells, BALB/c 3T3 fibroblasts transfected with the neomycin resistance gene) endogenously expressing NS5, as well as 18Neo cells pulsed with P17 or P17FDA, but not the control targets, unpulsed or P18IIIB pulsed 18Neo (FIG. 3).

Therefore, the CTL response generated with peptides of this invention is specific for target cells presenting processed products of endogenously synthesized NS5, not just exogenous peptide.

Figure 4:
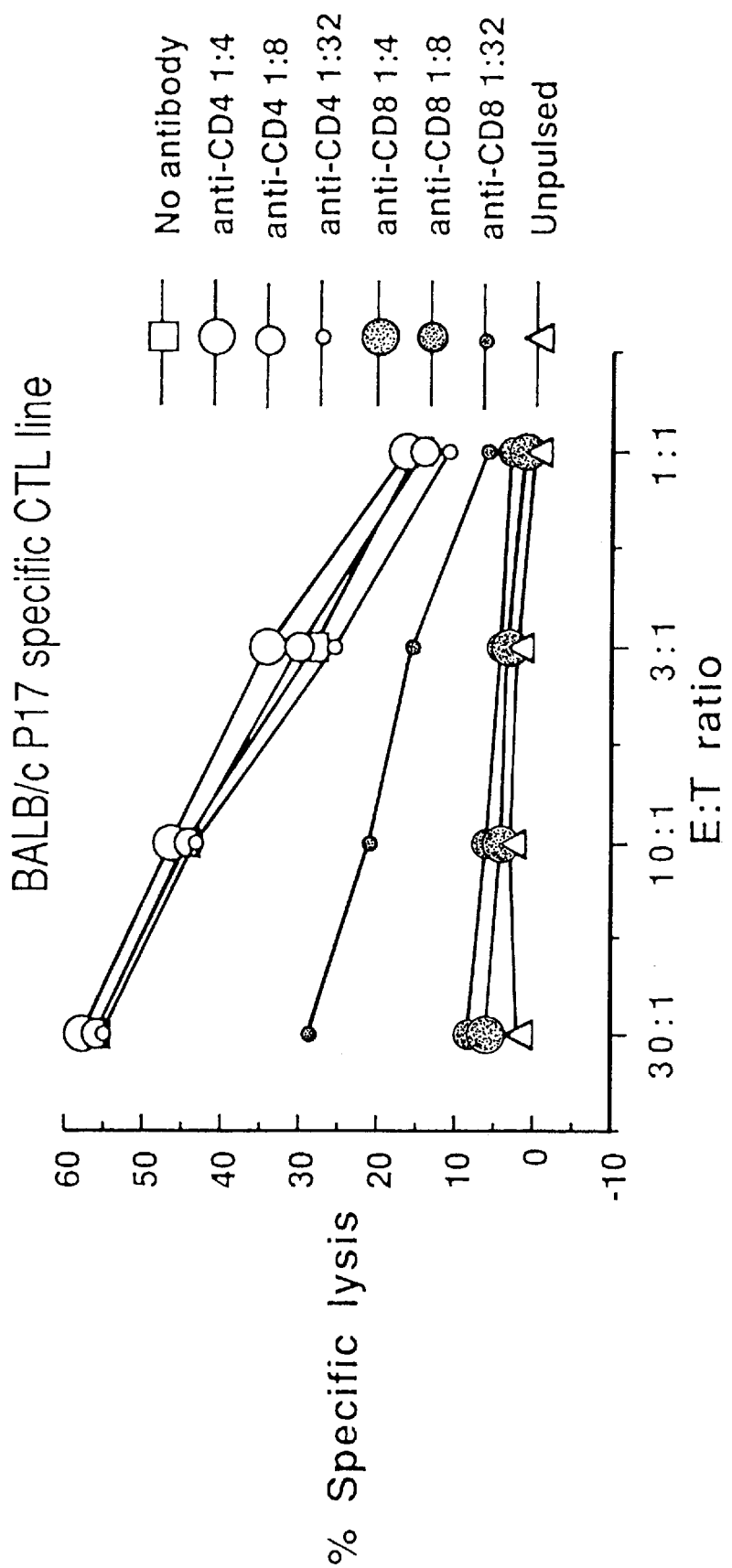
FIG. 4 shows an analysis of the phenotype of the H-$2^d$ CTL line specific for P17. The CTL assay, as described in FIG. 2, was performed in the presence of anti-L3T4 (GK 1.5) (anti-CD4) or anti-Lyt 2.2 (2.43) (anti-CD8) monoclonal antibodies (culture supernatant) at the indicated dilution, or no antibody, for 6 h. 18Neo was pulsed overnight with P17 (10 $\mu$M) and washed three times. Standard errors of triplicates were generally <5% of the values, and comparable results were obtained in three independent experiments.

Identification of T cell type by blocking of CTL response with antibodies. Treatment of the CTL cell lines specific for P17 with anti-CD8 monoclonal antibody, but not anti-CD4 antibody, reduced or abrogated cytotoxic activity on target cells (FIG. 4). Culture supernatant of hybridomas GK1.5 or 2.43 containing anti-L3T4 (anti-CD4, IgG2b (68) or anti-Lyt 2.2 (anti-CD8 (54)) antibodies, respectively, were added to the 96 well plates of CTL assay, at the indicated concentrations.

These results indicate that the effector cells which recognize P17 are conventional CD8$^+$CD4$^-$ (Lyt2$^+$L3T4$^-$) CTL. For H-2$^d$-restricted peptide-specific CTL lines in BALB/c, 18Neo cells expressing class I but not class II MHC gene products were used as targets. Therefore, these H-2$^d$ restricted CTL lines are likely to be class I MHC restricted, as expected for Lyt2$^+$ CD8$^+$ effector T cells. The P17FDA specific line showed similar results.

Identification of interacting domains of the MHC molecule using exon-shuffled and wild type class I transfectants. Transfectants expressing K$^d$, D$^d$, or L$^d$ molecules were used to determine which MHC molecule was specifically required for presentation of P17 in the H-2$^d$ context. Mouse L cell transfectants with D$^d$, L$^d$, or exon shuffles between these have been previously described (18,36,38,40) and were obtained from Dr. David Margulies, NIAID. The transfectant expressing K$^d$ was developed by Abastado et al. (1) and was obtained from Dr. Keiko Ozato (NICHD). All transfectant cell lines were examined by FACS analysis with an appropriate panel of anti-H-2D$^d$, anti-H-2K$^d$, and anti-H-2L$^d$ mAbs to confirm their expressed phenotype before the performance of the functional studies reported here.

The targets were pulsed with the indicated peptide and labeled with $^{51}$Cr at same time. T37.2.1 (α1α2 of D$^d$) and T4.8.3 (D$^d$) were found to present P17 nearly as well as the positive control cells (18neo BALB/c 3T3 fibroblasts) that express all three H-2$^d$ class I MHC molecules (FIG. 5). Neither K$^d$ nor L$^d$ nor any other D$^d$/L$^d$ exon-shuffled class I molecule presented P17 to the CTL.

Therefore the α1 and α2 domains were both necessary and together sufficient to present the peptide of this invention. Identical restriction was found for CTL recognizing P17FDA in BALB/c.

EXAMPLE 4

Provoking an Immune Response to NS5 Protein of Hepatitis C Virus by Administering a Peptide from Hepatitis C Virus NS5 Protein to a Mammal Formulation of a vaccine and immunization regimen. Peptide immunization with synthetic peptides to induce CD8+ CTL can be performed using 50–100 μg of peptide in complete or incomplete Freund's adjuvant according to the methods of Aichele, P., et al., *J. Exp. Med.* 171:1815–1820 (1990) or Kast, W. K., et al., *Proc Natl Acad Sci USA* 88:2283–2287 (1991), or on spleen cells, by the method of Harty, J. T., et al., *J. Exp. Med.* 175:1531–1538 (1992). Protection against viral or bacterial infections can be achieved by CTL induced by either of these immunization procedures.

It will be apparent to those skilled in the art that various modifications and variations can be made to the compositions of matter and methods of this invention. Thus, it is intended that the present invention cover the modifications and variations of this invention provided they come within the scope of the appended claims and their equivalents.

For purposes of completing the background description and present disclosure, each of the published articles, patents and patent applications heretofore identified in this specification are hereby incorporated by reference into the specification in their entirety.

The following documents have been cited in the specification as indicated by insertion of the following reference numbers in parentheses.

1. Abastado, J. -P., C. Jaulin, M. -P. Schutze, P. Langlade-Demoyen, F. Plata, K. Ozato, and P. Kourilsky. 1987. Fine mapping of epitopes by intradomain $K^d/D^d$ recombinants. *J. Exp. Med.* 166:327–340.
2. Alter, H. J., R. H. Purcell, J. W. Shih, J. C. Melpolder, M. Houghton, Q. -L. Choo, and G. Kuo. 1989. Detection of antibody to hepatitis C virus in prospectively followed transfusion recipients with acute and chronic non-A, non-B hepatitis. *N. Engl. J. Med.* 321:1494–1500.
3. Bangham, C. R. M., P. J. M. Openshaw, L. A. Ball, A. M. Q. King, G. W. Wertz, and B. A. Askonas. 1986. Human and murine cytotoxic T cells specific to respiratory syncytial virus recognize the viral nucleoprotein (N), but not the major glycoprotein (G), expressed by vaccinia virus recombinants. *J. Immunol.* 137:3973–3977.
4. Benacerraf, B. 1978. A hypothesis to relate the specificity of T lymphocytes and the activity of I region-specific Ir genes in macrophages and B lymphocytes. *J. Immunol.* 120:1809–1812.
5. Berzofsky, J. A. 1991. Approaches and issues in the development of vaccines against HIV. *J. Acq. Immune Defic. Syndromes* 4:451–459.
6. Bradley, D. W., K. A. McCaustland, E. H. Cook, C. A. Schable, J. W. Ebert, and J. E. Maynard. 1985. Posttransfusion non-A, non-B hepatitis in chimpanzees: physicochemical evidence that the tubule-forming agent is a small, enveloped virus. *Gastroenterology* 88:773–779.
7. Chakrabarti, S., M. Robert-Guroff, F. Wong-Staal, R. C. Gallo, and B. Moss. 1986. Expression of the HTLV-III envelope gene by a recombinant vaccinia virus. *Nature* 320:535–537.
8. Choo, Q. -L., G. Kuo, A. J. Weiner, L. R. Overby, D. W. Bradley, and M. Houghton. 1989. Isolation of a cDNA clone derived from blood-borne non-A, non-B viral hepatitis genome. *Science* 244:359–362.
9. Christiano, K., A. M. Di Bisceglie, J. H. Hoofnagle, and S. M. Feinstone. 1991. Hepatitis C viral RNA in serum of patients with chronic non-A, non-B hepatitis\: detection by the polymerase chain reaction using multiple primer sets. Hepatology 14:51–55.
10. Clerici, M., D. R. Lucey, R. A. Zajac, R. N. Boswell, H. M. Gebel, H. Takahashi, J. Berzofsky, and G. M. Shearer. 1991. Detection of cytotoxic T lymphocytes specific for synthetic peptides of gp160 in HIV-seropositive individuals. *J. Immunol.* 146:2214–2219.
11. Collett, N. S., V. Moennig, and M. C. Horzinek. 1989. Recent advances in pestivirus research. *J. Gen. Virol.* 70:253–266.
12. Cornette, J. L., H. Margalit, C. DeLisi, and J. A. Berzofsky. 1989. Concepts and methods in the identification of T cell epitopes and their use in the construction of synthetic vaccines. *Methods in Enzymol.* 178:611–634.
13. Cornette, J. L., H. Margalit, C. DeLisi, and J. A. Berzofsky. 1992. The amphipathic Helix as a structural feature involved in T-cell recognition, R. M. Epand (ed.), The Amphipathic Helix. CRC Press, Boca Raton, in press.
14. Culmann, B., E. Gomard, M. -P. KiÄny, B. Guy, F. Dreyfus, A. -G. Saimot, D. Sereni, D. Sicard, and J. -P. Lévy. 1991. Six epitopes reacting with human cytotoxic $CD8^+$ T cells in the central region of the HIV-1 nef protein. *J. Immunol.* 146:1560–1565.
15. DeLisi, C. and J. A. Berzofsky. 1985. T cell antigenic sites tend to be amphipathic structures. *Proc. Natl. Acad. Sci. U.S.A.* 82:7048–7052.
16. Di Bisceglie, A. M. and J. H. Hoofnagle. 1991. Therapy of chronic hepatitis C with a-interferon: The answer? Or more questions? *Hepatology* 13:601–603.
17. Earl, P. L., B. Moss, R. P. Morrison, K. Wehrly, J. Nishio, and B. Chesebro. 1986. T-Lymphocyte Priming and Protection Against Friend Leukemia by Vaccinia-Retrovirus env Gene Recombinant. *Science* 234:728.
18. Evans, G. A., D. H. Margulies, B. Shykind, J. G. Seidman, and K. Ozato. 1982. Exon shuffling: mapping polymorphic determinants on hybrid mouse transplantation antigens. *Nature* 300:755–757.
19. Feinstone, S. M., H. J. Alter, H. P. Dienes, Y. Shimizu, H. Popper, D. Blackmore, D. Sly, W. T. London, and R. H. Purcell. 1981. Non-A, non-B hepatitis in chimpanzees and marmosets. *J. Infect. Dis.* 144:588–598.
20. Gammon, G., J. Klotz, D. Ando, and E. E. Sercarz. 1990. The T cell repertoire to a multideterminant antigen: Clonal heterogeneity of the T cell response, variation between syngeneic individuals, and in vitro selection of the T cell specificities. *J. Immunol.* 144:1571–1577.
21. Goudsmit, J., C. Debouck, R. H. Neleon, L. Smit, M. Bakker, D. M. Asher, A. V. Wolff, C. J. Gibbs,Jr., and D. C. Gajdusek. 1988. Human immunodeficiency virus type 1 neutralization epitope with conserved architecture elicits early type-specific antibodies in experimentally infected chimpanzees. *Proc. Natl. Acad. Sci. U.S.A.* 85:4478–4482.
22. He, L. -F., D. Alling, T. Popkin, M. Shapiro, H. J. Alter, and R. H. Purcell. 1987. Determining the size of non-A, non-B hepatitis virus by filtration. *J. Infect. Dis.* 156:636–640.
23. Hijikata, M., N. Kato, Y. Ootsuyama, M. Nakagawa, S. Ohkoshi, and K. Shimotohno. 1991. Hypervariable regions in the putative glycoprotein of hepatitis C virus. *Biochem. Biophys. Res. Commun.* 175:220–228.
24. Hosmalin, A., M. Clerici, R. Houghten, C. D. Pendleton, C. Flexner, D. R. Lucey, B. Moss, R. N. Germain, G. M.

Shearer, and J. A. Berzofsky. 1990. An epitope in HIV-1 reverse transcriptase recognized by both mouse and human CTL. *Proc. Natl. Acad. Sci. U.S.A.* 87:2344–2348.

25. Houghten, R. A. 1985. General method for the rapid solid-phase synthesis of large numbers of peptides: specificity of antigen-antibody interaction at the level of individual amino acids. *Proc. Natl. Acad. Sci. U.S.A.* 82:5131–5135.

26. Houghton, M., Q. -L. Choo, and G. Kuo. 1988. NANBV diagnostics and vaccines. European Patent Application 88310922.

27. Houghton, M., A. Weiner, J. Han, G. Kuo, and Q. -L. Choo. 1991. Molecular biology of the hepatitis C viruses: implications for diagnosis, development and control of viral disease. *Hepatology* 14:381–388.

28. Imawari, M., M. Nomura, T. Kaieda, T. Moriyama, K. Oshimi, I. Nakamura, T. Gunji, S. Ohnishi, T. Ishikawa, H. Nakagama, and F. Takaku. 1989. Establishment of a human T-cell clone cytotoxic for both autologous and allogeneic hepatocytes from chronic hepatitis patients with type non-A, non-B virus. *Proc. Natl. Acad. Sci. USA* 86:2883–2887.

29. Kato, N., M. Hijikata, Y. Ootsuyama, M. Nakagawa, S. Ohkoshi, T. Sugimura, and K. Shimotohno. 1990. Molecular cloning of the human hepatitis C virus genome from Japanese patients with non-A, non-B hepatitis. *Proc. Natl Acad. Sci. USA* 87:9524–9528.

30. Kees, U. and P. H. Krammer. 1984. Most influenza A virus-specific memory cytotoxic T lymphocytes react with antigenic epitopes associated with internal virus determinants. *J. Exp. Med.* 159:365–377.

31. Kiyosawa, K., T. Sodeyama, E. Tanaka, Y. Gibo, K. Yoshizawa, Y. Nakano, S. Furuta, Y. Akahane, K. Nishioka, R. H. Purcell, and H. J. Alter. 1990. Interrelationship of blood transfusion, non-A, non-B hepatitis and heptacellular carcinoma\: analysis by detection of antibody to hepatitis C virus. *Hepatology* 12:671–675.

32. Koenig, S., T. R. Fuerst, L. V. Wood, R. M. Woods, J. A. Suzich, G. M. Jones, V. F. De la Cruz, R. T. Davey, Jr., S. Venkatesan, B. Moss, W. E. Biddison, and A. S. Fauci. 1990. Mapping the fine specificity of a cytolytic T cell response to HIV-1 nef protein. *J. Immunol.* 145:127–135.

33. Kuo, G., Q. -L. Choo, H. J. Alter, G. L. Gitnick, A. G. Redeker, R. H. Purcell, T. Miyamura, J. L. Dienstag, M. J. Alter, C. E. Stevens, G. E. Tegtmeier, F. Bonino, M. Colombo, W. -S. Lee, C. Kuo, K. Berger, J. R. Shuster, L. R. Overby, D. W. Bradley, and M. Houghton. 1989. An assay for circulating antibodies to a major etiologic virus of human non-A, non-B hepatitis. *Science* 244:362–364.

34. Liang, T. J., K. Hasegawa, N. Rimon, J. R. Wands, and E. Ben-Porath. 1991. A hepatitis B virus mutant associated with an epidemic of fulminant hepatitis. N. Engl. J. Med. 324:1705–1709.

35. Margalit, H., J. L. Spouge, J. L. Cornette, K. Cease, C. DeLisi, and J. A. Berzofsky. 1987. Prediction of immunodominant helper T-cell antigenic sites from the primary sequence. *J. Immunol.* 138:2213–2229.

36. Margulies, D. H., G. A. Evans, K. Ozato, R. D. Camerini-Otero, K. Tanaka, E. Appella, and J. G. Seidman. 1983. Expression of H-2D$^d$ and H-2L$^d$ mouse major histocompatibility antigen genes in L cells after DNA-mediated gene transfer. *J. Immunol.* 130:463.

37. Manéo, M., K. Kaminaka, H. Sugimoto, M. Esumi, N. Hayashi, K. Komatsu, K. Abe, S. Sekiguchi, M. Yano, K. Mizuno, and T. Shikata. 1990. A cDNA clone closely associated with non-A, non-B hepatitis. *Nucleic Acids Research* 18:2685–2689.

38. McCluskey, J., L. Boyd, M. Foo, J. Forman, D. H. Margulies, and J. A. Bluestone. 1986. Analysis of hybrid H-2D and L antigens with reciprocally mismatched aminoterminal domains: functional T cell recognition requires preservation of fine structural determinants. *J. Immunol.* 137:3881–3890.

39. Mondelli, M., G. M. Vergani, A. Alberti, D. Vergani, B. Portmann, A. L. W. F. Eddleston, and R. Williams. 1982. Specificity of T lymphocyte cytotoxicity to autologus hepatocytes in chronic hepatitis B virus infection: evidence that T cells are directed against HBV core antigen expressed on hepatocytes. *J. Immunol.* 129:2773–2778.

40. Murre, C., E. Choi, J. Weis, J. G. Seidman, K. Ozato, L. Liu, S. J. Burakoff, and C. S. Reiss. 1984. Dissection of serological and cytolytic T lymphocyte epitopes on murine major histocompatibility antigens by a recombinant H-2 gene separating the first two external domains. *J. Exp. Med.* 160:167–178.

41. Myers, G., S. F. Josephs, J. A. Berzofsky, A. B. Rabson, T. F. Smith, and F. Wong-Staal. 1989. Human retroviruses and AIDS 1989. Los Alamos National Laboratory, New Mexico.

42. Naumov, N. V., M. Mondelli, G. J. M. Alexander, R. S. Tedder, A. L. W. F. Eddleston, and R. Williams. 1984. Relationship between expression of hepatitis B virus antigens in isolated hepatocytes and autologous lymphocyte cytotoxicity in patients with chronic hepatitis B virus infection. *Hepatology* 4:63–68.

43. Nixon, D. F., A. R. M. Townsend, J. G. Elvin, C. R. Rizza, J. Gallwey, and A. J. McMichael. 1988. HIV-1 gag-specific cytotoxic T lymphocytes defined with recombinant vaccinia virus and synthetic peptides. *Nature* 336:484–487.

44. Ogata, N., H. J. Alter, R. H. Miller, and R. H. Purcell. 1991. Nucleotide sequence and mutation rate of the H strain of hepatitis C virus. *Proc. Natl. Acad. Sci. USA* 88:3392–3396.

45. Omata, M., T. Ehata, O. Yokosuka, K. Hosoda, and M. Ohto. 1991. Mutations in the precore region of hepatitis B virus DNA in patients with fulminant and severe hepatitis. *N. Engl. J. Ned.* 324:1699–1704.

46. Palker, T. J., M. E. Clark, A. J. Langlois, T. J. Matthews, K. J. Weinhold, R. R. Randall, D. P. Bolognesi, and B. F. Haynes. 1988. Type-specific neutralization of the human immunodeficiency virus with antibodies to env-encoded synthetic peptides. *Proc. Natl. Acad. Sci. U.S.A.* 85:1932–1936.

47. Pasternack, M. S. 1988. Cytotoxic T-lymphocytes. *Adv. Intern. Med.* 33:17–44.

48. Plata, F., P. Langlade-Demoyen, J. P. Abastado, T. Berbar, and P. Kourilsky. 1987. Retrovirus Antigens Recognized by Cytolytic T lymphocytes Activate Tumor Rejection In Vivo. *Cell* 48:231–240.

49. Puddington, L., M. J. Bevan, J. K. Rose, and L. Lefrancois. 1986. N protein is the predominant antigen recognized by vesicular stomatitis virus-specific cytotoxic T cells. *J. Virol.* 60:708–717.

50. Realdi, G., A. Alberti, M. Rugge, A. M. Rigoli, F. Tremolada, L. Schivazappa, and A. Ruol. 1982. Long-term follow-up of acute and chronic non-A, non-B post-transfusion hepatitis: evidence of progression to liver cirrhosis. *Gut* 23:270–275.

51. Rosenthal, A. S. 1978. Determinant selection and macrophage function in genetic control of the immune response. *Immunol. Rev.* 40:136–152.

52. Rouse, B. T., S. Norley, and S. Martin. 1988. Antiviral cytotoxic T lymphocyte induction and vaccination. *Rev. Infect. Dis.* 10:16–33.

53. Rusche, J. R., K. Javaherian, C. McDanal, J. Petro, D. L. Lynn, R. Grimaila, A. Langlois, R. C. Gallo, L. O. Arthur, P. J. Fischinger, D. P. Bolognesi, S. D. Putney, and T. J. Matthews. 1988. Antibodies that inhibit fusion of HIV infected cells bind a 24 amino acid sequence of the viral envelope, gp120. *Proc. Natl. Acad. Sci. U.S.A.* 85:3198–3202.

54. Sarmiento, M., A. L. Glasebrook, and F. W. Fitch. 1980. IgG or IgM monoclonal antibodies reactive with different determinants on the molecular complex bearing Lyt 2 antigen block T cell-mediated cytolysis in the absence of complement. *J. Immunol.* 125:2665–2672.

55. Schwartz, R. H. 1985. T-lymphocyte recognition of antigen in association with gene products of the major histocompatibility complex. *Annu. Rev. Immunol.* 3:237–261.

56. Shirai, M., C. D. Pendleton, and J. A. Berzofsky. 1992. Broad recognition of cytotoxic T-cell epitopes from the HIV-1 envelope protein with multiple class I histocompatibility molecules. *J. Immunol.* 148: 1657–1667.

57. Takahashi, H., J. Cohen, A. Hosmalin, K. B. Cease, R. Houghten, J. Cornette, C. DeLisi, B. Moss, R. N. Germain, and J. A. Berzofsky. 1988. An immunodominant epitope of the HIV gp160 envelope glycoprotein recognized by class I MHC molecule-restricted murine cytotoxic T lymphocytes. *Proc. Natl. Acad. Sci. USA* 85:3105–3109.

58. Takahashi, H., R. Houghten, S. D. Putney, D. H. Margulies, B. Moss, R. N. Germain, and J. A. Berzofsky. 1989. Structural requirements for class-I MHC molecule-mediated antigen presentation and cytotoxic T-cell recognition of an immunodominant determinant of the HIV envelope protein. *J. Exp. Med.* 170:2023–2035.

59. Takahashi, H., S. Merli, S. D. Putney, R. Houghten, B. Moss, R. N. Germain, and J. A. Berzofsky. 1989. A single amino acid interchange yields reciprocal CTL specificities for HIV gp160. *Science* 246:118–121.

60. Takamizawa, A., C. Mori, I. Fuke, S. Manabe, S. Murakami, J. Fujita, E. Onishi, T. Andoh, I. Yoshida, and H. Okayama. 1991. Structure and organizaton of the hepatitis C virus genome isolated from human carriers. *J. Virol.* 65:1105–1113.

61. Townsend, A. and H. Bodmer. 1989. Antigen recognition by class I-restricted T lymphocytes. *Annu. Rev. Immunol.* 7:601–624.

62. Townsend, A. RM., J. Rothbard, F. M. Gotch, G. Bahadur, D. Wraith, and A. J. McMichael. 1986. The epitopes of influenza nucleoprotein recognized by cytotoxic T lymphocytes can be defined with short synthetic peptides. *Cell* 44:959–968.

63. Tsubota, H., C. I. Lord, D. I. Watkins, C. Morimoto, and N. L. Letvin. 1989. A cytotoxic T lymphocyte inhibits acquired immunodeficiency syndrome virus replication in peripheral blood lymphocytes. *J. Exp. Med.* 169:1421–1434.

64. Van der Poel, C. L., H. T. M. Cuypers, H. W. Reesink, A. J. Weiner, S. Quan, R. Di Nello, J. J. P. Van Boven, I. Winkel, D. Mulder-Folkerts, P. J. Exel-Oehlers, W. Schaasberg, A. Leentvaar-Kuypers, A. Polito, M. Houghton, and P. N. Lelie. 1991. Confirmation of hepatitis C virus infection by new four-antigen recombinant immunoblot assay. *Lancet* 337:317–319.

65. Walker, B. D., C. Flexner, K. Birch-Limberger, L. Fisher, T. J. Paradis, A. Aldovini, R. Young, B. Moss, and R. T. Schooley. 1989. Long-term culture and fine specificity of human cytotoxic T lymphocyte clones reactive with human immunodeficiency virus type 1. *Proc. Natl. Acad. Sci. U.S.A.* 86:9514–9518.

66. Walker, C. M., D. J. Moody, D. P. Stites, and J. A. Levy. 1986. $CD8^+$ lymphocytes can control HIV infection in vitro by suppressing virus replication. *Science* 234:1563–1566.

67. Weiner, A. J., M. J. Brauer, J. Rosenblatt, K. H. Richman, J. Tung, K. Crawford, F. Bonino, G. Saracco, Q. -L. Choo, M. Houghton, and J. H. Han. 1991. Variable and hypervariable domains are found in the regions of HCV corresponding to the flavivirus envelope and NS1 proteins and the pestivirus envelope glycoproteins. *Virology* 180:842–848.

68. Wilde, D. B., P. Marrack, J. Kappler, D. P. Dialynas, and F. W. Fitch. 1983. Evidence implicating L3T4 in class II MHC antigen reactivity; monoclonal antibody GK1.5 (ANTI-L3T4a) blocks class II MHC antigen-specific proliferation, release of lymphokines, and binding by cloned murine helper T lymphocyte lines. *J. Immunol.* 131:2178–2183.

69. Yewdell, J. W., J. R. Bennink, G. L. Smith, and B. Moss. 1985. Influenza A virus nucleoprotein is a major target antigen for cross-reactive anti-influenza A virus cytotoxic T lymphocytes. *Proc. Natl. Acad. Sci. U.S.A.* 82:1785–1789.

70. Zinkernagel, R. M. and P. C. Doherty. 1979. MHC-restricted cytotoxic T cells: studies on the biological role of polymorphic major transplantation antigens determining T-cell restriction-specificity, function, and responsiveness. *Adv. Immunol.* 27:51–177.

71. Horacio, U. S., D. Fitzpatrick, A. Raktabutr, H. Nakanishi, M. Kahn and N. I. Greene. Design and synthesis of a mimetic from an antibody complementarity-determining region. *Science* 253:792–794 (1991).

What is claimed is:

1. A peptide that comprises a first segment of at least 8 consecutive residues from a sequence selected from the group consisting of MSYSWTGALVTPCAAE (SEQ ID NO: 1), MSYTWTGALVTPCAAE (SEQ ID NO: 2) and MSYTWTGALITPCAAE (SEQ ID NO: 3), such that said segment is a T cell epitope that induces a cytotoxic T cell response in lymphocytes of a mammal against cells that express hepatitis C virus NS5 protein, wherein said peptide is at least 8 residues and less than 50 residues in length.

2. A peptide according to claim 1, further comprising a second segment that is another T cell epitope.

3. A peptide according to claim 1, further comprising a second segment that is a B cell epitope.

4. A peptide according to claim 1, further comprising, at a terminus of said peptide, a linker and, affixed to said linker, a substance selected from the group consisting of a label, a solid matrix and a protein carrier.

5. A peptide according to claim 1, further comprising an agent conjugated to said peptide that provokes an immune response.

6. A method of detecting in lymphocytes of a mammal cytotoxic T cells that respond to a T cell epitope of NS5 protein of hepatitis C virus, comprising the steps of:
    (a) contacting target cells with a peptide according to claim 1, wherein said target cells are MHC-compatible with lymphocytes to be tested for said cytotoxic T cells;
    (b) contacting said lymphocytes to be tested for said cytotoxic T cells with a peptide according to claim 1; and
    (c) determining whether said lymphocytes exert a cytotoxic effect on said target cells, thereby indicating the presence of said lymphocytes that recognize a T-cell epitope of NS5 protein of hepatitis C virus.

7. A method of provoking in a mammal an immune response to NS5 protein of hepatitis C virus, comprising administering to said mammal an amount of a peptide according to claim 1 that is effective for inducing a cytotoxic T cell response against cells expressing hepatitis C virus NS5 protein.

* * * * *

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 16 amino acids
      (B) TYPE: amino acid
      (D) TOPOLOGY: linear (xi) SEQUENCE DESCRIPTION: SEQ ID NO:1:

Met Ser Tyr Ser Trp Thr Gly Ala Leu Val Thr Pro Cys Ala Ala Glu
1               5                   10                  15

(2) INFORMATION FOR SEQ ID NO:2:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:2:

Met Ser Tyr Thr Trp Thr Gly Ala Leu Val Thr Pro Cys Ala Ala Glu
1               5                   10                  15

(2) INFORMATION FOR SEQ ID NO:3:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:3:

Met Ser Tyr Thr Trp Thr Gly Ala Leu Ile Thr Pro Cys Ala Ala Glu
1               5                   10                  15

(2) INFORMATION FOR SEQ ID NO:4:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:4:

Arg Arg Leu His Gln Trp Ile Ser Ser Glu Cys Thr Thr Pro Cys Ser
1               5                   10                  15

Gly Ser Trp Leu
            20

(2) INFORMATION FOR SEQ ID NO:5:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:5:

Thr Thr Pro Cys Ser Gly Ser Trp Leu Arg Asp Ile Trp Asp Trp Ile
1               5                   10                  15

Cys Glu Val Leu
            20

(2) INFORMATION FOR SEQ ID NO:6:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:6:

Trp Asp Trp Ile Cys Glu Val Leu Ser Asp Phe Lys Thr Trp Leu Lys
1               5                   10                  15

Ala Lys Leu Met
            20

(2) INFORMATION FOR SEQ ID NO:7:

(i) SEQUENCE CHARACTERISTICS:
            (A) LENGTH: 20 amino acids
            (B) TYPE: amino acid
            (D) TOPOLOGY: linear (xi) SEQUENCE DESCRIPTION: SEQ ID NO:7:

Gly Thr Met Arg Ile Val Gly Pro Arg Thr Cys Arg Asn Met Trp Ser
    1               5                   10                  15

Gly Thr Phe Pro
                20

(2) INFORMATION FOR SEQ ID NO:8:

(i) SEQUENCE CHARACTERISTICS:
            (A) LENGTH: 20 amino acids
            (B) TYPE: amino acid
            (D) TOPOLOGY: linear (ix) FEATURE:
            (A) NAME/KEY: Modified-site
            (B) LOCATION: 12
            (D) OTHER INFORMATION: /note= "Xaa at positon 12 can be
                Gln or Arg"

(ix) FEATURE:
            (A) NAME/KEY: Modified-site
            (B) LOCATION: 20
            (D) OTHER INFORMATION: /note= "Xaa at position 20 can be
                Thr or Ser"

(xi) SEQUENCE DESCRIPTION: SEQ ID NO:8:

Arg Val Ser Ala Glu Glu Tyr Val Glu Ile Arg Xaa Val Gly Asp Phe
    1               5                   10                  15

His Tyr Val Xaa
                20

(2) INFORMATION FOR SEQ ID NO:9:

(i) SEQUENCE CHARACTERISTICS:
            (A) LENGTH: 20 amino acids
            (B) TYPE: amino acid
            (D) TOPOLOGY: linear (ix) FEATURE:
            (A) NAME/KEY: Modified-site
            (B) LOCATION: 15
            (D) OTHER INFORMATION: /note= "Xaa at positon 15 can be
                Thr or Ser"

(xi) SEQUENCE DESCRIPTION: SEQ ID NO:9:

Glu Tyr Val Glu Ile Arg Gln Val Gly Asp Phe His Tyr Val Xaa Gly
    1               5                   10                  15

Met Thr Thr Asp
                20

(2) INFORMATION FOR SEQ ID NO:10:

(i) SEQUENCE CHARACTERISTICS:
            (A) LENGTH: 20 amino acids
            (B) TYPE: amino acid
            (D) TOPOLOGY: linear (ix) FEATURE:
            (A) NAME/KEY: Modified-site
            (B) LOCATION: 4
            (D) OTHER INFORMATION: /note= "Xaa at position4 can be Val
                or Ile"

(xi) SEQUENCE DESCRIPTION: SEQ ID NO:10:

Pro Cys Gln Xaa Pro Ser Pro Glu Phe Phe Thr Glu Leu Asp Gly Val

```
                 1               5              10              15

Arg Leu His Arg
                           20

(2) INFORMATION FOR SEQ ID NO:11:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:11:

Pro Ser Pro Glu Phe Phe Thr Glu Leu Asp Gly Val Arg Leu His Arg
    1               5                  10                  15

Phe Ala Pro Pro
                20

(2) INFORMATION FOR SEQ ID NO:12:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:12:

Val Ala Val Leu Thr Ser Met Leu Thr Asp Pro Ser His Ile Thr Ala
    1               5                  10                  15

(2) INFORMATION FOR SEQ ID NO:13:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:13:

Ile Thr Ala Glu Ala Ala Gly Arg Arg Leu Ala Arg Gly Ser Pro
    1               5                  10                  15

(2) INFORMATION FOR SEQ ID NO:14:

(i) SEQUENCE CHARACTERISTICS:
        (A) LENGTH: 20 amino acids
        (B) TYPE: amino acid
        (D) TOPOLOGY: linear (ix) FEATURE:
        (A) NAME/KEY: Modified-site
        (B) LOCATION: 3
        (D) OTHER INFORMATION: /note= "Xaa at position 3 can be
            Ala or Glu"

(xi) SEQUENCE DESCRIPTION: SEQ ID NO:14:

Glu Arg Xaa Ile Ser Val Pro Ala Glu Ile Leu Arg Lys Ser Arg Arg
    1               5                  10                  15

Phe Ala Gln Ala
                20

(2) INFORMATION FOR SEQ ID NO:15:

(i) SEQUENCE CHARACTERISTICS:
        (A) LENGTH: 20 amino acids
        (B) TYPE: amino acid
        (D) TOPOLOGY: linear (ix) FEATURE:
        (A) NAME/KEY: Modified-site
        (B) LOCATION: 1
```

(D) OTHER INFORMATION: /note= "Xaa at position 1 can be
    Ala or Glu"

(xi) SEQUENCE DESCRIPTION: SEQ ID NO:15:

Xaa Ile Ser Val Pro Ala Glu Ile Leu Arg Lys Ser Arg Arg Phe Ala
1               5                   10                  15

Gln Ala Leu Pro
            20

(2) INFORMATION FOR SEQ ID NO:16:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:16:

Leu Thr Glu Ser Thr Leu Ser Thr Ala Leu Ala Glu Leu Ala Thr Arg
1               5                   10                  15

Ser Phe Gly Ser
            20

(2) INFORMATION FOR SEQ ID NO:17:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:17:

Ala Thr Arg Ser Phe Gly Ser Ser Thr Ser Gly Ile Thr Gly
1               5                   10                  15

(2) INFORMATION FOR SEQ ID NO:18:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:18:

Glu Gln Lys Leu Pro Ile Asn Ala Leu Ser Asn Ser Leu Leu Arg His
1               5                   10                  15

His Asn (2) INFORMATION FOR SEQ ID NO:19:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO:19:

Leu Gln Val Leu Asp Ser His Tyr Gln Asp Val Leu Lys Glu Val Lys
1               5                   10                  15

Ala Ala Ala Ser Lys
            20

(2) INFORMATION FOR SEQ ID NO:20:

(i) SEQUENCE CHARACTERISTICS:
        (A) LENGTH: 20 amino acids
        (B) TYPE: amino acid
        (D) TOPOLOGY: linear (ix) FEATURE:

(A) NAME/KEY: Modified-site
           (B) LOCATION: 2
           (D) OTHER INFORMATION: /note= "Xaa at positon 2 can be Ala
               or Val"

(ix) FEATURE:
           (A) NAME/KEY: Modified-site
           (B) LOCATION: 20
           (D) OTHER INFORMATION: /note= "Xaa at position 20 can be
               Asn or Ser"

(xi) SEQUENCE DESCRIPTION: SEQ ID NO:20:

His Xaa Arg Lys Ala Val Thr His Ile Asn Ser Val Trp Lys Asp Leu
    1               5                  10                  15

Leu Glu Asp Xaa
                20

(2) INFORMATION FOR SEQ ID NO:21:

(i) SEQUENCE CHARACTERISTICS:
           (A) LENGTH: 20 amino acids
           (B) TYPE: amino acid
           (D) TOPOLOGY: linear (ix) FEATURE:
           (A) NAME/KEY: Modified-site
           (B) LOCATION: 3
           (D) OTHER INFORMATION: /note= "Xaa at position 3 can be
               Thr or Ala"

(ix) FEATURE:
           (A) NAME/KEY: Modified-site
           (B) LOCATION: 16
           (D) OTHER INFORMATION: /note= "Xaa at position 16 can be
               Asn or Ser"

(ix) FEATURE:
           (A) NAME/KEY: Modified-site
           (B) LOCATION: 17
           (D) OTHER INFORMATION: /note= "Xaa at positon 17 can be
               Val or Phe"

(xi) SEQUENCE DESCRIPTION: SEQ ID NO:21:

Ala Val Xaa His Ile Asn Ser Val Trp Lys Asp Leu Leu Glu Asp Xaa
    1               5                  10                  15

Xaa Thr Pro Ile
                20

(2) INFORMATION FOR SEQ ID NO:22:

(i) SEQUENCE CHARACTERISTICS:
           (A) LENGTH: 16 amino acids
           (B) TYPE: amino acid
           (D) TOPOLOGY: linear (xi) SEQUENCE DESCRIPTION: SEQ ID NO:22:

Pro Asp Leu Gly Val Arg Val Cys Glu Lys Met Ala Leu Tyr Asp Val
    1               5                  10                  15

(2) INFORMATION FOR SEQ ID NO:23:

(i) SEQUENCE CHARACTERISTICS:
           (A) LENGTH: 15 amino acids
           (B) TYPE: amino acid
           (D) TOPOLOGY: linear (ix) FEATURE:
           (A) NAME/KEY: Modified-site
           (B) LOCATION: 8
           (D) OTHER INFORMATION: /note= "Xaa at position 8 can be
               Thr or Ser"

(xi) SEQUENCE DESCRIPTION: SEQ ID NO:23:

Met Ala Leu Tyr Asp Val Val Xaa Lys Leu Pro Leu Ala Val Met
1               5                   10                  15

(2) INFORMATION FOR SEQ ID NO:24:

(i) SEQUENCE CHARACTERISTICS:
      (A) LENGTH: 16 amino acids
      (B) TYPE: amino acid
      (D) TOPOLOGY: linear (xi) SEQUENCE DESCRIPTION: SEQ ID NO:24:

Gln Ala Arg Val Ala Ile Lys Ser Leu Thr Glu Arg Leu Tyr Val Gly
1               5                   10                  15

(2) INFORMATION FOR SEQ ID NO:25:

(i) SEQUENCE CHARACTERISTICS:
      (A) LENGTH: 19 amino acids
      (B) TYPE: amino acid
      (D) TOPOLOGY: linear (xi) SEQUENCE DESCRIPTION: SEQ ID NO:25:

Ala Ser Gly Val Leu Thr Thr Ser Cys Gly Asn Thr Leu Thr Cys Tyr
1               5                   10                  15

Ile Lys Ala (2) INFORMATION FOR SEQ ID NO:26:

(i) SEQUENCE CHARACTERISTICS:
      (A) LENGTH: 16 amino acids
      (B) TYPE: amino acid
      (D) TOPOLOGY: linear (ix) FEATURE:
      (A) NAME/KEY: Modified-site
      (B) LOCATION: 3
      (D) OTHER INFORMATION: /note= "Xaa at position 3 can be
          Cys or Arg"

(xi) SEQUENCE DESCRIPTION: SEQ ID NO:26:

Ala Ala Xaa Arg Ala Ala Gly Leu Gln Asp Cys Thr Met Leu Val Cys
1               5                   10                  15

(2) INFORMATION FOR SEQ ID NO:27:

(i) SEQUENCE CHARACTERISTICS:
      (A) LENGTH: 20 amino acids
      (B) TYPE: amino acid
      (D) TOPOLOGY: linear (ix) FEATURE:
      (A) NAME/KEY: Modified-site
      (B) LOCATION: 14
      (D) OTHER INFORMATION: /note= "Xaa at position 14 can be
          Ala or Val"

(ix) FEATURE:
      (A) NAME/KEY: Modified-site
      (B) LOCATION: 20
      (D) OTHER INFORMATION: /note= "Xaa at positon 20 can be
          Ala or Val"

(xi) SEQUENCE DESCRIPTION: SEQ ID NO:27:

Val Gln Glu Asp Ala Ala Ser Leu Arg Ala Phe Thr Glu Xaa Met Thr
1               5                   10                  15

Arg Tyr Ser Xaa
                20

(2) INFORMATION FOR SEQ ID NO:28:

(i) SEQUENCE CHARACTERISTICS:
        (A) LENGTH: 20 amino acids
        (B) TYPE: amino acid
        (D) TOPOLOGY: linear (ix) FEATURE:
        (A) NAME/KEY: Modified-site
        (B) LOCATION: 12
        (D) OTHER INFORMATION: /note= "Xaa at position 12 can be
            Ala or Val"

(xi) SEQUENCE DESCRIPTION: SEQ ID NO:28:

Arg Ala Phe Thr Glu Ala Met Thr Arg Tyr Ser Xaa Pro Pro Gly Asp
    1            5                    10               15

Pro Pro Gln Pro
            20

(2) INFORMATION FOR SEQ ID NO:29:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:29:

His Thr Pro Val Asn Ser Trp Leu Gly Asn Ile Ile Met
    1            5                    10

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: linear (ix) FEATURE:
        (A) NAME/KEY: Modified-site
        (B) LOCATION: 4
        (D) OTHER INFORMATION: /note= "Xaa at position 4 can be
            Gly or Ala"

(ix) FEATURE:
        (A) NAME/KEY: Modified-site
        (B) LOCATION: 12
        (D) OTHER INFORMATION: /note= "Xaa at position 12 can be
            Leu or Val"

(xi) SEQUENCE DESCRIPTION: SEQ ID NO:30:

Glu Ile Tyr Xaa Ala Cys Tyr Ser Ile Glu Pro Xaa Asp Leu Pro
    1            5                    10               15